United States Patent
Jamison et al.

(10) Patent No.: US 9,642,833 B2
(45) Date of Patent: *May 9, 2017

(54) VITAMIN C AND VITAMIN K, AND COMPOSITIONS THEREOF FOR TREATMENT OF OSTEOLYSIS OR PROLONGATION OF PROSTHETIC IMPLANT

(71) Applicant: IC-MEDTECH CORPORATION, Las Vegas, NV (US)

(72) Inventors: James M. Jamison, Stow, OH (US); Thomas M. Miller, Las Vegas, NV (US); Deborah R. Neal, Uniontown, OH (US); Mark William Kovacik, Mogadore, OH (US); Michael John Askew, Strongsville, OH (US); Richard Albert Mostardi, Ravenna, OH (US)

(73) Assignee: IC-MEDTECH CORPORATION, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/716,587

(22) Filed: May 19, 2015

(65) Prior Publication Data

US 2015/0250760 A1  Sep. 10, 2015

Related U.S. Application Data

(63) Continuation of application No. 13/384,574, filed as application No. PCT/US2010/042427 on Jul. 19, 2010, now Pat. No. 9,050,265.

(60) Provisional application No. 61/227,041, filed on Jul. 20, 2009.

(51) Int. Cl.

| A61K 31/34 | (2006.01) |
|---|---|
| A61K 31/11 | (2006.01) |
| A61K 31/375 | (2006.01) |
| A61K 9/00 | (2006.01) |
| A61K 9/08 | (2006.01) |
| A61K 9/20 | (2006.01) |
| A61K 9/48 | (2006.01) |
| A61K 31/122 | (2006.01) |
| A61K 45/06 | (2006.01) |
| A61K 31/185 | (2006.01) |

(52) U.S. Cl.
CPC .......... *A61K 31/375* (2013.01); *A61K 9/0019* (2013.01); *A61K 9/08* (2013.01); *A61K 9/2054* (2013.01); *A61K 9/48* (2013.01); *A61K 9/4866* (2013.01); *A61K 31/122* (2013.01); *A61K 31/185* (2013.01); *A61K 45/06* (2013.01)

(58) Field of Classification Search
CPC ............................. A61K 31/375; A61K 31/12
USPC .................................................. 514/474, 682
See application file for complete search history.

(56) References Cited

U.S. PATENT DOCUMENTS

| 6,468,414 | B1 | 10/2002 | Mahdavi et al. |
|---|---|---|---|
| 6,599,945 | B2 | 7/2003 | Docherty et al. |
| 7,091,241 | B2 | 8/2006 | Gilloteaux et al. |
| 7,094,809 | B2 | 8/2006 | Docherty et al. |
| 9,050,265 | B2 * | 6/2015 | Jamison .............. A61K 9/0019 |
| 2002/0146463 | A1 | 10/2002 | Clayton |
| 2003/0073738 | A1 | 4/2003 | Gilloteaux et al. |
| 2007/0043110 | A1 | 2/2007 | Gilloteaux et al. |
| 2008/0081041 | A1 | 4/2008 | Nemeth |
| 2010/0056625 | A1 | 3/2010 | Miller et al. |
| 2011/0028436 | A1 | 2/2011 | Greenwald |
| 2011/0160301 | A1 | 6/2011 | Tsai et al. |

FOREIGN PATENT DOCUMENTS

| CN | 101537174 | 9/2009 |
|---|---|---|
| JP | 2006131611 A | 5/2006 |
| WO | 0247493 A2 | 6/2002 |
| WO | 2007147128 A2 | 12/2007 |
| WO | 2009118726 A2 | 10/2009 |

OTHER PUBLICATIONS

Dypbukt et al., "Different prooxidant levels stimulate growth, trigger apoptosis, or produce necrosis of insulin-secreting RINm5F cells," J. Biol. Chem., 1994, 269, 30553-30560.

Sata et al., "Menadione induces both necrosis and apoptosis in rat pancreatic acinar AR4-2J cells," Free Radic. Biol. Med., 1997, 23, 844-850.

Jamison et al., "Cell cycle arrest and autoschizis in a human bladder carcinoma cell line following vitamin C and vitamin K3 treatment," Biochem. Pharm., 2004, 67, 337-351.

Wang et al., "Effects of vitamin C on androgen receptor mediated actions in human prostate adenocarcinoma cell line LAPC-4," Urology, 2003, 62, 167-171.

De Laurenzi et al., "Cell death by oxidative stress and ascorbic acid regeneration in human neuroectodermal cell lines," Eur. J. Cancer, 1995, 31, 463-466.

Noto et al., "Effects of sodium ascorbate (vitamin C) and 2-methyl-1,4-naphthoquinone (vitamin K3) treatment on human tumor cell growth in vitro," Cancer, 1989, 63, 901-906.

Buc Calderon et al., "Potential therapeutic application of the association of vitamins C and K3 in cancer treatment," Curr. Med. Chem., 2002, 9, 2269-2285.

Venugopal et al., "Synergistic antitumor activity of vitamins C and K3 against human prostate carcinoma cell lines," Cell Biol. Int., 1996, 20, 787-797.

Venugopal et al., "Synergistic antitumor activity of vitamin C and K3 on human urologic tumor cell lines," Life Sci., 1996, 59, 1389-1400.

(Continued)

Primary Examiner — Raymond Henley, III
(74) Attorney, Agent, or Firm — Jones Day

(57) ABSTRACT

Provided herein is a method of treating, preventing, or managing osteolysis in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof.

25 Claims, 3 Drawing Sheets

(56) References Cited

OTHER PUBLICATIONS

Kassouf et al., "Vitamins C and K3 sensitize human urothelial tumors to gemcitabine," J. Urol., 2006, 176, 1642-1647.

Jamison et al., "Flow cytometric and ultrastructural aspects of the synergistic antitumor activity of vitamin C and vitamin K3 combinations against prostatic carcinoma cells," Tissue Cell, 1996, 28, 687-701.

Lisanti et al., "Hydrogen peroxide fuels aging, inflammation, cancer metabolism and metastasis: the seed and soil also needs 'fertilizer'," Cell Cycle, 2011, 10, 2440-2449.

Bijur et al., "Antimutagenic and promutagenic activity of ascorbic acid during oxidative stress," Environ. Mol. Mutagen., 1997, 30, 339-345.

Bijur et al., "Ascorbic acid dehydroascorbate induces cell cycle arrest at G2/M DNA damage checkpoint during oxidative stress," Environ. Mol. Mutagen., 1999, 33, 144-152.

Juan et al., "Vitamin K3 inhibits growth of human hepatoma HepG2 cells by decreasing activities of both p34CDC2 kinase and phosphatase," Biochem. Biophys. Res. Commun., 1993, 190, 907-913.

Gelvan et al., "Sites and mechanisms of low-level oxidative stress in cultured cells," Biochem. Biophys. Res. Commun., 1995, 206, 421-428.

Chen et al., "Involvement of Rb family proteins, focal adhesion proteins and protein synthesis in senescent morphogenesis induced by hydrogen peroxide," J. Cell Sci., 2000, 113, 4087-4097.

Beck et al., "Ascorbate/menadione-induced oxidative stress kills cancer cells that express normal or mutated forms of the oncogenic protein Bcr-Abl. An in vitro and in vivo mechanistic study," Invest. New Drugs, 2011, 29, 891-900.

Vita et al., "Pankiller effect of prolonged exposure to menadione on glioma cells: potentiation by vitamin C," Invest. New Drugs, 2011, 29, 1314-1320.

"Exploring Apatone®," SummaMagzine, Fall 2010, 6-12.

Jamison et al., "The in vitro and in vivo antitumor activity of vitamin C: K3 combinations against prostate cancer," Trends in Prostate Cancer Research, 2005, Editor: John Lucas, pp. 189-236.

Bullough, "Metallosis," J. Joint Bone Surg. Br., 1994, 76, 687-688.

Rae, "The toxicity of metals used in orthopaedic prostheses. An experimental study using cultured human synovial fibroblasts," J. Joint Bone Surg. Br., 1981, 63, 435-440.

Kovacik et al., "Osteolytic indicators found in total knee arthroplasty synovial fluid aspirates," Clin. Orthop. Relat. Res., 2003, 379, 186-194.

Tuan et al., "What are the local and systemic biologic reactions and mediators to wear debris, and what host factors determine or modulate the biologic response to wear particles?," J. Am. Acad. Orthop. Surg., 2008, 16, S42-S48.

CARPENTER et al., "Receptors for epidermal growth factor and other polypeptide mitogens," Ann. Rev. Biochem., 1987, 56, 881-914.

Mostardi et al., "In vitro response of human fibroblasts to commercially pure titanium," J. Biomed. Mater. Res., 1999, 47, 60-64.

Mostardi et al., "Prosthetic metals have a variable necrotic threshold in human fibroblasts: an in vitro study," J. Biomed. Mater. Res., 2002, 59, 605-610.

Kovacik et al., "Differences in the surface composition of seemingly similar F75 cobalt-chromium micron-sized particulates can affect synovial fibroblast viability," Colloids Surf. B Biointerfaces, 2008, 65, 269-275.

Summa Health Systems, "Call for Applications-2008 Summer Research Fellowship Program," Feb. 1, 2008, pp. 1-18.

Verrax et al., "The association of vitamins C and K3 kills cancer cells mainly by autoschizis, a novel form of cell death. Basis for their potential use as coadjuvants in anticancer therapy," Eur. J. Med. Chem., 2003, 38, 451-457.

Clohisy et al., "NF-kB signaling blockade abolishes implant particle-induced osteoclastogenesis," J. Orthop. Res. 2004, 22, 13-20.

Gilloteaux et al., "Cell damage and death by autoschizis in human bladder (RT4) carcinoma cells resulting from treatment with ascorbate and menadione," Untrastruct. Pathol., 2010, 34, 140-160 (XP009153018).

Tareen et al, "A 12 week, open label, phase I/IIa study using apatone for the treatment of prostate cancer patients who have failed standard therapy," Int. J. Med. Sci. 2008, 5, 62-67.

Carcamo et al., "Vitamin C suppresses TNF alpha-induced NF kappa B activation by inhibiting I kappa B alpha phosphorylation," Biochemistry, 2002, 41, 12995-13002.

Faloon, "Protection against arterial calcification, bone loss, cancer, and aging," LifeExtension Magazine, 2009, 1-15 (XP-002661706).

Osada et al., "The utility of vitamin K3 (menadione) against pancreatic cancer," Anticancer Res., 2008, 28, 45-50.

Ozaki et al., "Menatetrenone, a vitamin K2 analogue, inhibits hepatocellular carcinoma cell growth by suppressing cyclin D1 expression through inhibition of nuclear factor kappaB activation," Clin. Cancer Res. 2007, 13, 2236-2245.

Neal et al., "Apatone® Treatment Inhibits the Inflammatory Response in Human Synovial, Fibroblasts Following Metal Particulate Exposure by Reducing NF-κB Levels," Microsc. Microanal., 2009, 15, 894-895 (XP009152986).

Mostardi et al., "A comparison of the effects of prosthetic and commercially pure metals on retrieved human fibroblasts: the role of surface elemental composition," Acta Biomater. 2010, 6, 702-707.

Sugiyama et al., "Role of physiological antioxidants in chromium(VI)-induced cellular injury," Free Radic. Biol. Med., 1992, 12, 397-401.

Summa Health System: "New Awards and Presentations," (XP002661708).

Kovacik, "Apatone: The benefits in joint replacement," Orthopaedic Focus, Winter 2010 (XP002661709).

Shah et al., "The use of Apatone® as an inhibitor of necrosis following prosthetic particulate challenge of human synovial fibroblasts," Summa Health System Summer Research Fellowship Poster Day, Jul. 25, 2008.

Kovacik et al., "Apatone® treatment reduces NFkB levels of synovial fibroblasts following metal particulate exposure," The 55th Annual Meeting of the Orthopaedic Research Society, Feb. 22-25, 2009, Poster #2384.

Kovacik et al., "Apatone® treatment enhances cell proliferation and reduces inflammation following cobalt-chrome exposure," The 2009 Annual Meeting and Exposition, Society for Biomaterials, Apr. 22-25, Poster #507.

Kovacik et al., "A novel drug treatment enhances cell proliferation while reducing the inflammatory response following cobalt-chromium exposure," An internal presentation at Summa Health System Community of Research, Mar. 27, 2009.

Jamison et al., "Liquid crystalline compounds as pharmaceuticals," Summa Health System Research Forum, Sep. 25, 2009, C3.

McGuire et al., "Elucidating the pathway of Apatone® induced DNase II reactivation during autoschizic cell death," Summa Health System Research Forum, Sep. 25, 2009, C4.

Kovacik et al., "A novel drug treatment enhances cell proliferation while reducing the inflammatory response following cobalt-chromium exposure," Summa Health System Research Forum, Sep. 25, 2009, C5.

Tsai et al., "Structure-activity relationship analysis of phenolic compounds with antioxidant, anti-inflammatory, and anticancer activities," Summa Health System Research Forum, Sep. 25, 2009, P76.

Jamison et al., "Redistribution of fibrillarin following treatment of human bladder carcinoma cells with Apatone®," Summa Health System Research Forum, Sep. 25, 2009, P78.

Jamison et al., "Apatone® exhibits antitumor activity against prostate cancer," Summa Health System Research Forum, Sep. 25, 2009, P79.

Jamison et al., "Induction of cell cycle arrest and autoschizis in a human bladder carcinoma cell line by vitamins C and K3," Summa Health System Research Forum, Sep. 25, 2009, P80.

(56) References Cited

OTHER PUBLICATIONS

Allen et al., "The effects of particulate cobalt, chromium and cobalt-chromium alloy on human osteoblast-like cells in vitro," J. Bone Joint Surg., 1997, 79-B, 475-482.

Hallab et al., "Differential lymphocyte reactivity to serum-derived metal—protein complexes produced from cobalt-based and titanium-based implant alloy degradation," J Biomed. Mater. Res., 2001, 56, 427-436.

Difara, "The remarkable anticancer properties of vitamin K," LifeExtension Magazine, Nov. 2010.

Jana et al., "Autoschizis of T-cells is induced by the nutritional supplement, Cr(III)picolinate," Toxicology in Vitro, 2010, 24, 586-596.

Messer and Lucas, "Evaluations of metabolic activities as biocompatibility tools: a study of individual ions' effects on fibroblasts," Dental Materials, 1999, 15, 1-6.

Carlisle et al., "Apoptosis and P53 induction in human lung fibroblasts exposed to chromium (VI): Effect of ascorbate and tocopherol," Toxicological Sciences, 2000, 55, 60-68.

Taper and Roberfroid, "Cancer chemotherapy protentiation induced by combined vitamin C and K3 with ferrous sulfate pretreatment," Oncol. (Life Sci. Adv.), 1992, 11, 19-25.

Caicedo et al., "Analysis of metal ion-induced DNA damage, apoptosis, and necrosis in human (Jurkat) T-cells demonstrates Ni2+ and V3+ are more toxic than other metals: Al3+, Be2+, Co2+, Cr3+, Cu2+, Fe3+, Mo5+, Nb5+, Zr2+," J. Biomed. Mater. Res., 2008, 86A, 905-913.

Caicedo et al., "Soluble and particulate Co—Cr—Mo alloy implant metals activate the inflammasome danger signaling pathway in human macrophages: A novel mechanism for implant debris reactivity," J. Orthop. Res., 2009, 27, 847-854.

Urban et al., "Dissemination of wear particles to the liver, spleen, and abdominal lymph nodes of patients with hip or knee replacement," J. Bone Joint Surg. Am., 2000, 82, 457-477.

Hallab et al., "Th1 type lymphocyte reactivity to metals in patients with total hip arthroplasty," J. Orthop. Surg. Res., 2008, 3, 6.

Brown et al., "Sensitivity to metal as a possible cause of sterile loosening after cobalt-chromium total hip-replacement arthroplasty," J. Bone Joint Surg. Am., 1977, 59, 164-168.

Ferguson et al., "The ionization of metal implants in living tissues," J. Bone Joint Surg. Am., 1960, 42, 77-90.

Hallab et al., "Concentration—and composition-dependent effects of metal ions on human MG-63 osteoblasts," J. Biomed. Mater. Res., 2002, 60, 420-433.

Deheer et al., "In situ complement activation by polyethylene wear debris," J. Biomed. Mater. Res., 2001, 54, 12-19.

Surat, "Isolation of prostaglandin E2-like material from osteonecrosis induced by steroids and its prevention by kallikrein-inhibitor, aprotinin. An experimental study in rabbits," Prostaglandins Leukot. Med. 1984, 13, 159-167.

Kido et al., "Disease-specific expression patterns of proteases in synovial tissues," Pathol. Res. Pract., 2007, 203, 451-456.

* cited by examiner

VITAMIN C AND VITAMIN K, AND COMPOSITIONS THEREOF FOR TREATMENT OF OSTEOLYSIS OR PROLONGATION OF PROSTHETIC IMPLANT

CROSS REFERENCE TO RELATED APPLICATIONS

This application is a continuation of U.S. application Ser. No. 13/384,574, now U.S. Pat. No. 9,050,265, which is the National Stage of International Application No. PCT/US2010/042427, filed Jul. 19, 2010, which claims the benefit of U.S. Provisional Application No. 61/227,041, filed Jul. 20, 2009, the disclosure of each of which is incorporated herein by reference in its entirety.

FIELD

Provided herein is a method of treating, preventing, or managing osteolysis in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof.

BACKGROUND

Prosthetic joint replacement is a common surgical procedure with at least 1 million joint replacements being implanted each year worldwide (Bullough, *J. Joint Bone Surg.* (*Br*) 1994, 76, 687-688). However, approximately 10% of prosthetic joint replacements fail within 10 years. Most often these failures are attributed to a detrimental biological response triggered by the generation of fine metal wear particles that dislodge from the artificial implant surfaces during normal activities. Such biological response can cause an inflammatory irritation of the adjacent tissue and of the bone to which the implant is attached, causing debilitating pain to return, and in some instances, the need for a costly second restorative surgery (Bae, *J. Bone Joint Surg. B* 1981, 63, 435-440; Kovacik et al., *Clin. Orthop. Relat. Res.* 2003, 379, 186-194; and Tuan, *J. Am. Acd. Ortho. Surg.* 2008, 16, S42).

Therefore, there exists a need for effective therapies for prolonging the functional life of a prosthetic implant and treating aseptic osteolysis associated with a prosthetic implant.

SUMMARY OF THE DISCLOSURE

Provided herein is a method of treating, preventing, or managing osteolysis in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In one embodiment, the osteolysis is aseptic osteolysis. In another embodiment, the osteolysis is caused by inflammation. In yet another embodiment, the osteolysis is caused by a prosthetic implant in the subject. In yet another embodiment, the osteolysis is caused by particulate debris from the prosthetic implant in the subject. In certain embodiments, the subject is treated orally with a capsule that contains about 500 mg of sodium L-ascorbate and about 5 mg of sodium 1,2,3,4-tetrahydro-2-methyl-1,4-dioxo-2-naphthalenesulfonate. In yet another embodiment, the inflammation is related to or impacting the bone or cartilage or tissue related to the bone.

Also provided herein is a method of treating, preventing, or managing inflammation associated with a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In one embodiment, the inflammation is associated with particulate debris from the prosthetic implant in the subject. In certain embodiments, the subject is treated orally with a capsule that contains about 500 mg of sodium L-ascorbate and about 5 mg of sodium 1,2,3,4-tetrahydro-2-methyl-1,4-dioxo-2-naphthalenesulfonate.

Additionally provided is a method of treating, preventing, or managing inflammation caused by a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In one embodiment, the inflammation is caused by particulate debris from the prosthetic implant in the subject. In certain embodiments, the subject is treated orally with a capsule that contains about 500 mg of sodium L-ascorbate and about 5 mg of sodium 1,2,3,4-tetrahydro-2-methyl-1,4-dioxo-2-naphthalenesulfonate.

Further provided herein is a method of increasing the functional life of a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the subject is treated orally with a capsule that contains about 500 mg of sodium L-ascorbate and about 5 mg of sodium 1,2,3,4-tetrahydro-2-methyl-1,4-dioxo-2-naphthalenesulfonate.

Provided herein is a method of treating, preventing, or managing NFκB-mediated condition, disorder, or disease caused by a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the method of treating, preventing, or managing NFκB-mediated condition, disorder, or disease is caused by particulate debris from a prosthetic implant in the subject. In certain embodiments, the subject is treated orally with a capsule that contains about 500 mg of sodium L-ascorbate and about 5 mg of sodium 1,2,3,4-tetrahydro-2-methyl-1,4-dioxo-2-naphthalenesulfonate.

Provided herein is a method of reducing NFκB production in a cell exposed to prosthetic particulate debris, comprising contacting the cell with an effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof.

Provided herein is a method of enhancing proliferation of a cell exposed to prosthetic particulate debris, comprising contacting the cell with an effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof.

DETAILED DESCRIPTION

Figure 1:
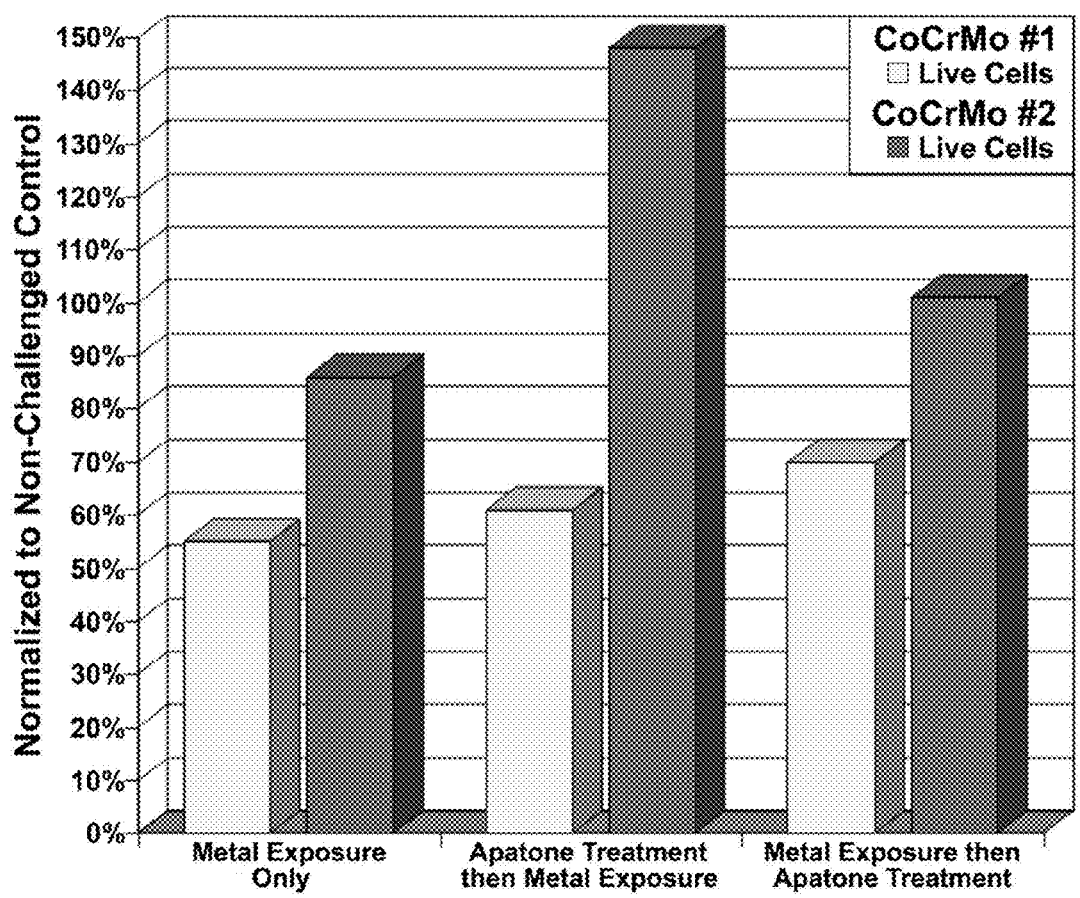
FIG. 1 shows the effect of APATONE® on cellular viability of human synovial fibroblasts exposed to metal particles.

To facilitate understanding of the disclosure set forth herein, a number of terms are defined below.

Generally, the nomenclature used herein and the laboratory procedures in organic chemistry, medicinal chemistry, biochemistry, biology, pharmacology, and others described herein are those well known and commonly employed in the art. Unless defined otherwise, all technical and scientific terms used herein generally have the same meaning as commonly understood by one of ordinary skill in the art to which this disclosure belongs.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "osteolysis" refers to dissolution or degeneration of bone tissue. In certain embodiments, the term "osteolysis" refers to dissolution or degeneration of bone tissue caused by prosthetic implant, including an active resorption or dissolution of the bone tissue as a part of an ongoing disease process.

The terms "nuclear factor kappa B" and "NFκB" are used interchangeably herein and refer to a member of the Rel family of transcription factors that contain the Rel homology (RH) domain, or variant thereof, as described, for example, in Carpenter et al., Ann. Rev. Biochem. 1987, 56, 881-914. Examples of NFκB include, but are not limited to, RelA (p65), c-Rel, p50, p52, and the Drosophila dorsal and Dif gene products. NFκB variants include proteins substantially homologous to a native NFκB, i.e., proteins having one or more naturally or non-naturally occurring amino acid deletions, insertions or substitutions (e.g., NFκB derivatives, homologs, and fragments), as compared to the amino acid sequence of a native NFκB. The amino acid sequence of a NFκB variant is at least about 80% identical, at least about 90% identical, or at least about 95% identical to a native NFκB. In certain embodiments, the NFκB is p65 or a variant thereof.

The terms "NFκB-mediated condition, disorder, or disease" and "a condition, disorder, or disease mediated by NFκB" refer to a condition, disorder, or disease characterized by inappropriate, e.g., less than or greater than normal, NFκB activity. Inappropriate NFκB functional activity might arise as the result of NFκB expression in cells which normally do not express NFκB, increased NFκB expression or degree of intracellular activation, leading to, e.g., inflammatory and immune-related disorders or diseases; or decreased NFκB expression. An NFκB-mediated condition, disorder, or disease may be completely or partially mediated by inappropriate NFκB activity. In certain embodiments, an NFκB-mediated condition, disorder, or disease is one in which modulation of the NFκB activity results in some effect on the underlying condition or disorder, e.g., a NFκB antagonist or agonist results in some improvement in at least some of patients being treated.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "manage," "managing," and "management" refer to preventing or slowing the progression, spread, or worsening of a condition, disorder, or disease, or of one or more symptoms (e.g., pain) thereof. Sometimes, the beneficial effects that a subject derives from a prophylactic or therapeutic agent do not result in a cure of the condition, disorder, or disease. In one embodiment, the term management refers to preventing or slowing the progression, spread, or worsening of the pain of osteolysis.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The terms "therapeutically effective amount" and "effective amount" are meant to include the amount of a compound or combination of compounds that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient"

refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "APATONE®" refers to a pharmaceutical composition which comprises L-ascorbate and 1,2,3,4-tetrahydro-2-methyl-1,4-dioxo-2-naphthalenesulfonate. In certain embodiments, the term "APATONE®" refers to a pharmaceutical composition, wherein the weight ratio of L-ascorbate to 1,2,3,4-tetrahydro-2-methyl-1,4-dioxo-2-naphthalenesulfonate is 100 or 200.

The term "alkyl" refers to a linear or branched saturated monovalent hydrocarbon radical, wherein the alkylene may optionally be substituted as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkenyl" refers to a linear or branched monovalent hydrocarbon radical, which contains one or more, in one embodiment, one to five, carbon-carbon double bonds. The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, carbon-carbon triple bonds. The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—CCH) and propargyl (—CH$_2$CCH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "optionally substituted" is intended to mean that a group, such as an alkyl, alkenyl, alkynyl, cycloalkyl, aryl, heteroaryl, heterocyclyl, or alkoxy group, may be substituted with one or more substituents independently selected from, e.g., (a) alkyl, alkenyl, alkynyl, cycloalkyl, aryl, aralkyl, heteroaryl, and heterocyclyl; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^b$ and R$^c$ together with the N atom to which they are attached form heteroaryl or heterocyclyl. As used herein, all groups that can be substituted are "optionally substituted," unless otherwise specified.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The term "chromium-free" refers to a chemical (e.g., a compound or composition) that contains no more than 100 ppm, 50 ppm, 20 ppm, 10 ppm, 5 ppm, 2 ppm, 1 ppm, 0.1 ppm, 10 bpm, or 1 bpm of chromium. In one embodiment, the term "chromium-free" refers to a chemical that contains no more than 10 ppm. In another embodiment, the term "chromium-free" refers to a chemical that contains no more than 5 ppm. In yet another embodiment, the term "chromium-free" refers to a chemical that contains no more than 2 ppm. In yet another embodiment, the term "chromium-free" refers to a chemical that contains no more than 1 ppm. In still another embodiment, the term "chromium-free" refers to a chemical that contains no more than 1 ppm. The chromium content can be determined using a conventional technique well known to one of ordinary skill in the art, e.g., inductively coupled plasma (ICP) technique.

Vitamin C

As used herein, the term "vitamin C" refers to L-ascorbic acid or a pharmaceutically acceptable salt thereof; or a pharmaceutically acceptable solvate or hydrate thereof. Vitamin C is also known as L-xyloascorbic acid, 3-oxo-L-gulofuranolactone (enol form), L-3-ketothreohexuronic acid lactone, antiscorbutic vitamin, cevitamic acid, adenex, allercorb, ascorin, ascorteal, ascorvit, cantan, cantaxin, catavin C, cebicure, cebion, cecon, cegiolan, celaskon, celin, cenetone, cereon, cergona, cescorbat, cetamid, cetabe, cetemican, cevalin, cevatine, cevex, cevimin, ce-vi-sol, cevitan, cevitex, cewin, ciamin, cipca, concemin, C-vin, daviamon C, duoscorb, hybrin, laroscorbine, lemascorb, planavit C, proscorbin, redoxon, ribena, scorbacid, scorbu-C, testascorbic, vicelat, vitacee, vitacimin, vitacin, vitascorbol, and xitix.

In one embodiment, vitamin C provided herein is L-ascorbic acid. In another embodiment, vitamin C provided herein is a pharmaceutically acceptable salt of L-ascorbic acid, or a pharmaceutically acceptable solvate or hydrate thereof.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In one embodiment, vitamin C provided herein is an alkali or alkaline earth metal salt of L-ascorbic acid, or a pharmaceutically acceptable solvate or hydrate thereof. In another embodiment, vitamin C provided herein is sodium, potassium, calcium, or magnesium L-ascorbate, or a pharmaceutically acceptable solvate or hydrate thereof. In yet another embodiment, vitamin C provided herein is sodium L-ascorbate, or a pharmaceutically acceptable solvate or hydrate thereof. In yet another embodiment, vitamin C provided herein is sodium L-ascorbate, which is also known as vitamin C sodium, ascorbin, sodascorbate, natrascorb, cenolate, ascorbicin, or cebitate. In yet another embodiment, vitamin C provided herein is potassium L-ascorbate, or a pharmaceutically acceptable solvate or hydrate thereof. In yet another embodiment, vitamin C provided herein is magnesium L-ascorbate, or a pharmaceutically acceptable solvate or hydrate thereof. In still another embodiment, vitamin C provided herein is magnesium L-ascorbate.

In certain embodiments, the vitamin C provided herein is D-ascorbic acid or a pharmaceutically acceptable salt, or a pharmaceutically acceptable solvate or hydrate thereof.

In certain embodiments, the vitamin C, or provided herein is chromium-free. In certain embodiments, the chromium-free vitamin C provided herein contains no more than 100 ppm, 50 ppm, 20 ppm, 10 ppm, 5 ppm, 2 ppm, 1 ppm, 0.1 ppm, 10 bpm, or 1 bpm of chromium. In certain embodiments, the chromium-free vitamin C provided herein contains no greater than 10 ppm chromium. In certain embodiments, the chromium-free vitamin C provided herein contains no greater than 5 ppm chromium. In certain embodiments, the chromium-free vitamin C provided herein contains no greater than 2 ppm chromium. In certain embodiments, the chromium-free vitamin C provided herein contains no greater than 1 ppm chromium.

Vitamin K

As used herein, the term "vitamin K" refers to a 2-methyl-1,4-naphthoquinone derivative of Formula I or II:

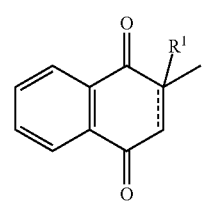

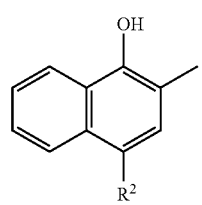

or an enantiomer, a mixture of enantiomers, or a mixture of two or more diastereomers thereof; or a pharmaceutically acceptable salt, solvate, or hydrate thereof; wherein $R^1$ is alkyl, alkenyl, alkynyl, or —$SO_3H$; and $R_2$ is hydroxyl or amino.

In certain embodiments, the vitamin K provided herein is vitamin $K_1$, vitamin $K_2$, vitamin $K_3$, vitamin $K_4$, or vitamin $K_5$, or a mixture thereof.

In one embodiment, the vitamin K provided herein is vitamin $K_1$, or a pharmaceutically acceptable salt, solvate, or hydrate thereof. Vitamin $K_1$ is also known as phylloquinone, [R—[R*,R*-(E)]]-2-methyl-3-(3,7,11,15-tetramethyl-2-hexadecenyl)-1,4-naphthalenedione, 2-methyl-3-phytyl-1,4-naphthoquinone, 3-phytylmenadione, phytomenadione, phytonadione, aqua-merphyton, konakion, mephyton, mono-day, veda-$K_1$, and veta-$K_1$.

In another embodiment, the vitamin K provided herein is vitamin $K_2$, or a pharmaceutically acceptable salt, solvate, or hydrate thereof. Vitamin $K_2$ is also known as menaquinones, 2-methyl-3-all-trans-polyprenyl-1,4-naphthoquinones. Some non-limiting examples of vitamin $K_2$ include menaquinone 4, which is also known as vitamin $K_{2(20)}$; menaquinone 6, which is also known as vitamin $K_{2(30)}$; and menaquinone 7, which is also known as vitamin $K_{2(35)}$.

In yet another embodiment, the vitamin K provided herein is vitamin $K_3$, or a pharmaceutically acceptable salt, solvate, or hydrate thereof. Vitamin $K_3$ is also known as menadione, 2-methyl-1,4-naphthalenedione, 2-methyl-1,4-naphthoquinone, menaphthone, vitamin $K_{2(0)}$, kanone, kappaxin, kayklot, kayquinone, klottone, kolklot, and thyloquinone, 1,2,3,4-tetrahydro-2-methyl-1,4-dioxo-2-naphthalenesulfonic acid, and sodium 1,2,3,4-tetrahydro-2-methyl-1,4-dioxo-2-naphthalenesulfonate.

In one embodiment, the vitamin K provided herein is 1,2,3,4-tetrahydro-2-methyl-1,4-dioxo-2-naphthalenesulfonic acid, or a pharmaceutically acceptable salt, solvate, or hydrate thereof. In another embodiment, the vitamin K provided herein is 1,2,3,4-tetrahydro-2-methyl-1,4-dioxo-2-naphthalenesulfonate (also known as menadione bisulfite), or a pharmaceutically acceptable solvate or hydrate thereof. Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In one embodiment, vitamin $K_3$ provided herein is an alkali or alkaline earth metal salt of 1,2,3,4-tetrahydro-2-methyl-1,4-dioxo-2-naphthalenesulfonic acid, or a pharmaceutically acceptable solvate or hydrate thereof. In another embodiment, vitamin $K_3$ provided herein is sodium, potassium, calcium, or magnesium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is sodium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is potassium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is magnesium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is sodium 1,2,3,4-tetrahydro-2-methyl-1,4-dioxo-2-naphthalenesulfonate. In yet another embodiment, vitamin $K_3$ provided herein is anhydrous sodium 1,2,3,4-tetrahydro-2-methyl-1,4-dioxo-2-naphthalenesulfonate. In yet another embodiment, vitamin $K_3$ provided herein is sodium 1,2,3,4-tetrahydro-2-methyl-1,4-dioxo-2-naphthalenesulfonate hydrate. In still another embodiment, vitamin $K_3$ provided herein is sodium 1,2,3,4-tetrahydro-2-methyl-1,4-dioxo-2-naphthalenesulfonate trihydrate.

In certain embodiments, the vitamin K provided herein is vitamin $K_4$, or a pharmaceutically acceptable salt, solvate, or hydrate thereof. Vitamin $K_4$ is also known as menadiol, 2-methyl-1,4-naphthalenediol, 2-methyl-1,4-naphthohydroquinone, 2-methyl-1,4-naphthoquinol, and dihydrovitamin $K_3$.

In certain embodiments, the vitamin K provided herein comprises vitamin $K_3$ and vitamin $K_4$, or pharmaceutically acceptable salts, solvates, or hydrates thereof.

In certain embodiments, the vitamin K provided herein is vitamin $K_5$, or a pharmaceutically acceptable salt, solvate, or hydrate thereof. Vitamin $K_5$ is also known as 4-amino-2-methyl-1-naphthalenol, 4-amino-2-methyl-1-naphthol, 1-hydroxy-2-methyl-4-aminonaphalene, 2-methyl-4-amino-1-hydroxynaphthalene, 2-methyl-4-amino-1-naphthol, 3-methyl-4-hydroxy-1-naphthylamine, and synkamin.

In certain embodiments, the vitamin K provided herein is chromium-free. In certain embodiments, the chromium-free vitamin K provided herein contains no more than 100 ppm, 50 ppm, 20 ppm, 10 ppm, 5 ppm, 2 ppm, 1 ppm, 0.1 ppm, 10 bpm, or 1 bpm of chromium. In certain embodiments, the chromium-free vitamin K provided herein contains no greater than 10 ppm chromium. In certain embodiments, the chromium-free vitamin K provided herein contains no greater than 5 ppm chromium. In certain embodiments, the chromium-free vitamin K provided herein contains no greater than 2 ppm chromium. In certain embodiments, the chromium-free vitamin K provided herein contains no greater than 1 ppm chromium.

In certain embodiments, the vitamin K provided herein is chromium-free vitamin $K_3$. In certain embodiments, the chromium-free vitamin $K_3$ provided herein contains no more than 100 ppm, 50 ppm, 20 ppm, 10 ppm, 5 ppm, 2 ppm, 1 ppm, 0.1 ppm, 10 bpm, or 1 bpm of chromium. In certain embodiments, the chromium-free vitamin $K_3$ provided herein contains no greater than 10 ppm chromium. In certain embodiments, the chromium-free vitamin $K_3$ provided herein contains no greater than 5 ppm chromium. In certain embodiments, the chromium-free vitamin $K_3$ provided herein contains no greater than 2 ppm chromium. In certain embodiments, the chromium-free vitamin $K_3$ provided herein contains no greater than 1 ppm chromium.

In certain embodiments, the vitamin K provided herein is chromium-free sodium 1,2,3,4-tetrahydro-2-methyl-1,4-dioxo-2-naphthalenesulfonate. In certain embodiments, the chromium-free sodium 1,2,3,4-tetrahydro-2-methyl-1,4-dioxo-2-naphthalenesulfonate contains no more than 100 ppm, 50 ppm, 20 ppm, 10 ppm, 5 ppm, 2 ppm, 1 ppm, 0.1 ppm, 10 bpm, or 1 bpm of chromium. In certain embodiments, the chromium-free sodium 1,2,3,4-tetrahydro-2-methyl-1,4-dioxo-2-naphthalenesulfonate contains no greater than 10 ppm chromium. In certain embodiments, the chromium-free sodium 1,2,3,4-tetrahydro-2-methyl-1,4-dioxo-2-naphthalenesulfonate contains no greater than 5 ppm chromium. In certain embodiments, the chromium-free sodium 1,2,3,4-tetrahydro-2-methyl-1,4-dioxo-2-naphthalenesulfonate contains no greater than 2 ppm chromium. In certain embodiments, the chromium-free sodium 1,2,3,4-tetrahydro-2-methyl-1,4-dioxo-2-naphthalenesulfonate contains no greater than 1 ppm chromium.

In certain embodiments, the chromium-free vitamin $K_3$ provided herein is made via a cerium mediator electrochemical technology (CETECH™) as described in U.S. Pat. No. 6,468,414, the disclosure of which is incorporated by reference in its entirety. Alternatively, chromium-free vitamin $K_3$ is available from commercial sources, such as PRO-K™ (Lonza Group Ltd, Switzerland).

Pharmaceutical Compositions: a Combination of Vitamins C and K

In one embodiment, provided herein are pharmaceutical compositions comprising (a) vitamin C, or a pharmaceutically acceptable salt, solvate, or hydrate thereof, in combination with (b) vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture thereof.

In another embodiment, provided herein are pharmaceutical compositions comprising (a) vitamin C, or a pharmaceutically acceptable salt, solvate, or hydrate thereof, in combination with (b) chromium-free vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture thereof.

In yet another embodiment, provided herein are pharmaceutical compositions comprising (a) chromium-free vitamin C, or a pharmaceutically acceptable salt, solvate, or hydrate thereof, in combination with (b) chromium-free vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture thereof.

In still another embodiment, provided herein is a chromium-free pharmaceutical composition comprising (a) vitamin C, or a pharmaceutically acceptable salt, solvate, or hydrate thereof, in combination with (b) vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture thereof.

In certain embodiments, the pharmaceutical compositions provided herein are chromium-free. In certain embodiments, the pharmaceutical compositions provided herein contain no more than 100 ppm, 50 ppm, 20 ppm, 10 ppm, 5 ppm, 2 ppm, 1 ppm, 0.1 ppm, 10 bpm, or 1 bpm of chromium. In certain embodiments, the pharmaceutical compositions provided herein contains no greater than 10 ppm chromium. In certain embodiments, the pharmaceutical compositions provided herein contains no greater than 5 ppm chromium. In certain embodiments, the pharmaceutical compositions provided herein contains no greater than 2 ppm chromium. In certain embodiments, the pharmaceutical compositions provided herein contains no greater than 1 ppm chromium.

In one embodiment, the weight ratio of vitamin C to vitamin K in the pharmaceutical compositions provided herein is ranging from about 1 to about 500, from about 4 to about 500, from about 10 to about 500, from about 50 to about 500, from about 25 to about 250, or from about 50 to about 200, from about 50 to about 150, or from about 80 to about 120. In another embodiment, the weight ratio of vitamin C to vitamin K in the pharmaceutical compositions provided herein is about 1, about 2, about 4, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250. In yet another embodiment, the weight ratio of vitamin C to vitamin K in the pharmaceutical compositions provided herein is about 100. In still another embodiment, the weight ratio of vitamin C to vitamin K in the pharmaceutical compositions provided herein is about 200.

In one embodiment, the mole ratio of vitamin C to vitamin K in the pharmaceutical compositions provided herein is ranging from about 1 to about 500, from about 4 to about 500, from about 10 to about 500, from about 25 to about 250, or from about 50 to about 200, from about 50 to about 150, or from about 80 to about 120. In another embodiment, the mole ratio of vitamin C to vitamin K in the pharmaceutical compositions provided herein is about 1, about 2, about 4, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250. In yet another embodiment, the mole ratio of vitamin C to vitamin K in the pharmaceutical compositions provided herein is about 100. In still another embodiment, the mole ratio of vitamin C to vitamin K in the pharmaceutical compositions provided herein is about 200.

The pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (See, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions provided herein are formulated in a dosage form for oral administration. In another embodiment, the pharmaceutical compositions provided herein are formulated in a dosage form for parenteral administration. In yet another embodiment, the pharmaceutical compositions provided herein are formulated in a dosage form for intravenous administration. In yet another embodiment, the pharmaceutical compositions provided herein are formulated in a dosage form for topical administration. In still another embodiment, the pharmaceutical compositions provided herein are formulated in a dosage form for local injection.

In one embodiment, the pharmaceutical compositions provided herein are formulated together as a capsule. In one embodiment, the capsule contains from about 10 mg to about 1,000 mg, from about 25 mg to about 900 mg, from about 50 mg to about 800 mg, from about 100 mg to about 700 mg, from about 200 mg to about 600 mg, from about 300 mg to about 600 mg, or from about 400 mg to about 600 mg of vitamin C, or a pharmaceutically acceptable salt, solvate, or hydrate thereof; and from about 0.1 mg to about 10 mg, from about 1 mg to about 9 mg, from about 2 mg to about 8 mg, from about 3 mg to about 7 mg, or from about 4 mg to about 6 mg of vitamin K, or a single enantiomer, a mixture of enantiomers, or a mixture of diastereomers thereof, or a pharmaceutically acceptable salt, solvate, or hydrate thereof. In another embodiment, the capsule contains from about 400 mg to about 600 mg of vitamin C, or a pharmaceutically acceptable salt, solvate, or hydrate thereof; and from about 4 mg to about 6 mg of vitamin K, or a single enantiomer, a mixture of enantiomers, or a mixture of diastereomers thereof, or a pharmaceutically acceptable salt, solvate, or hydrate thereof. In yet another embodiment, the capsule contains about 200 mg, about 300 mg, about 400, about 500, about 600 mg, about 700 mg, about 800 mg, or about 900 mg of vitamin C, or a pharmaceutically acceptable salt, solvate, or hydrate thereof; and about 1 mg, about 2 mg, about 3 mg, about 4 mg, about 5 mg, about 6 mg, about 7 mg, about 8 mg, about 9 mg, or about 10 mg of vitamin K, or a single enantiomer, a mixture of enantiomers, or a mixture of diastereomers thereof, or a pharmaceutically acceptable salt, solvate, or hydrate thereof. In still another embodiment, the capsule contains about 500 mg of vitamin C, or a pharmaceutically acceptable salt, solvate, or hydrate thereof; and about 5 mg of vitamin K, or a single enantiomer, a mixture of enantiomers, or a mixture of diastereomers thereof, or a pharmaceutically acceptable salt, solvate, or hydrate thereof. In certain embodiments, the capsule consists essentially of vitamins C, or a pharmaceutically acceptable salt, solvate, or hydrate thereof; and K, or a single enantiomer, a mixture of enantiomers, or a mixture of diastereomers thereof, or a pharmaceutically acceptable salt, solvate, or hydrate thereof.

In one embodiment, vitamin C in the pharmaceutical compositions provided herein is L-ascorbic acid or a pharmaceutically acceptable salt thereof, or a pharmaceutically acceptable solvate or hydrate thereof. In another embodiment, vitamin C in the pharmaceutical compositions provided herein is an alkali or alkaline earth metal salt of L-ascorbic acid, or a pharmaceutically acceptable solvate or hydrate thereof. In yet another embodiment, vitamin C in the pharmaceutical compositions provided herein is sodium, potassium, calcium, or magnesium salt of L-ascorbic acid, or a pharmaceutically acceptable solvate or hydrate thereof. In yet another embodiment, vitamin C in the pharmaceutical compositions provided herein is sodium L-ascorbate. In still another embodiment, vitamin C in the pharmaceutical compositions provided herein is magnesium L-ascorbate.

In one embodiment, vitamin K in the pharmaceutical compositions provided herein is vitamin $K_3$, or a pharmaceutically acceptable salt, solvate, or hydrate thereof. In another embodiment, vitamin K in the pharmaceutical compositions provided herein is 1,2,3,4-tetrahydro-2-methyl-1,4-dioxo-2-naphthalenesulfonic acid, or a pharmaceutically acceptable salt, solvate, or hydrate thereof. In yet another embodiment, vitamin K in the pharmaceutical compositions provided herein is an alkali or alkaline earth metal salt of 1,2,3,4-tetrahydro-2-methyl-1,4-dioxo-2-naphthalenesulfonic acid, or a pharmaceutically acceptable solvate or hydrate thereof. In yet another embodiment, vitamin K in the pharmaceutical compositions provided herein is sodium, potassium, calcium, or magnesium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is sodium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is potassium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is magnesium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is sodium 1,2,3,4-tetrahydro-2-methyl-1,4-dioxo-2-naphthalenesulfonate. In yet another embodiment, vitamin K in the pharmaceutical compositions provided herein is anhydrous sodium 1,2,3,4-tetrahydro-2-methyl-1,4-dioxo-2-naphthalenesulfonate. In yet another embodiment, vitamin K in the pharmaceutical compositions provided herein is sodium 1,2,3,4-tetrahydro-2-methyl-1,4-dioxo-2-naphthalenesulfonate hydrate. In still another embodiment, vitamin K in the pharmaceutical compositions provided herein is sodium 1,2,3,4-tetrahydro-2-methyl-1,4-dioxo-2-naphthalenesulfonate trihydrate.

In one embodiment, the capsule contains about 500 mg of sodium L-ascorbate, and about 5 mg of sodium 1,2,3,4-tetrahydro-2-methyl-1,4-dioxo-2-naphthalenesulfonate or a hydrate thereof. In another embodiment, the capsule contains about 500 mg of magnesium L-ascorbate, and about 5 mg of sodium 1,2,3,4-tetrahydro-2-methyl-1,4-dioxo-2-naphthalenesulfonate or hydrate thereof. In yet another embodiment, the capsule contains about 500 mg of sodium L-ascorbate and about 5 mg of anhydrous sodium 1,2,3,4-tetrahydro-2-methyl-1,4-dioxo-2-naphthalenesulfonate. In yet another embodiment, the capsule contains about 500 mg of sodium L-ascorbate and about 5 mg of sodium 1,2,3,4-tetrahydro-2-methyl-1,4-dioxo-2-naphthalenesulfonate trihydrate. In yet another embodiment, the capsule contains about 500 mg of magnesium L-ascorbate and about 5 mg of anhydrous sodium 1,2,3,4-tetrahydro-2-methyl-1,4-dioxo-2-naphthalenesulfonate. In still another embodiment, the capsule contains about 500 mg of magnesium L-ascorbate and about 5 mg of sodium 1,2,3,4-tetrahydro-2-methyl-1,4-dioxo-2-naphthalenesulfonate trihydrate.

In one embodiment, the capsule consists essentially of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the capsule consists essentially of vitamin C, or a pharmaceutically acceptable salt, solvate, or hydrate thereof, in combination with vitamin $K_3$, or a pharmaceutically acceptable salt, solvate, or hydrate thereof. In one embodiment, the capsule consists essentially of sodium L-ascorbate, and sodium 1,2,3,4-tetrahydro-2-methyl-1,4-dioxo-2-naphthalenesulfonate or a hydrate thereof. In another embodiment, the capsule consists essentially of magnesium L-ascorbate, and sodium 1,2,3,4-tetrahydro-2-methyl-1,4-dioxo-2-naphthalenesulfonate or hydrate thereof. In yet another embodiment, the capsule consists essentially of sodium L-ascorbate and anhydrous sodium 1,2,3,4-tetrahydro-2-methyl-1,4-dioxo- 2-naphthalenesulfonate. In yet another embodiment, the capsule consists essentially of sodium L-ascorbate and sodium 1,2,3,4-tetrahydro-2-methyl-1,4-dioxo-2-naphthalenesulfonate trihydrate. In yet another embodiment, the capsule consists essentially of magnesium L-ascorbate and anhydrous sodium 1,2,3,4-tetrahydro-2-methyl-1,4-dioxo-2-naphthalenesulfonate. In still another embodiment, the capsule consists essentially of magnesium L-ascorbate and sodium 1,2,3,4-tetrahydro-2-methyl-1,4-dioxo-2-naphthalenesulfonate trihydrate.

The pharmaceutical compositions provided herein can also be formulated as known to those skilled in the art. Some examples of vitamins C and K containing pharmaceutical compositions are described in U.S. Pat. No. 7,091,241, which is incorporated herein by reference in its entirety.

The pharmaceutical compositions provided herein may be provided in a unit-dosage or multiple-dosage form. A unit-dosage form, as used herein, refers to physically discrete a unit suitable for administration to a subject, e.g., a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409, 239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (*theobroma* oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(-)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

In one embodiment, provided herein is a method of treating, preventing, or managing a pseudotumor in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the pseudotumor is polycystic kidney disease. In certain embodiments, the pseudotumor is polycystic liver disease. In certain embodiments, the pseudotumor is aseptic osteolysis.

In one embodiment, provided herein is a method of treating, preventing, or managing osteolysis in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In one embodiment, the osteolysis is aseptic osteolysis. In another embodiment, the osteolysis is caused by inflammation. In yet another embodiment, the osteolysis is caused by a prosthetic implant in the subject. In yet another embodiment, the osteolysis is caused by particulate debris from the prosthetic implant in the subject. In certain embodiments, the combination of vitamins C and K has a synergetic effect in treating, preventing, or managing osteolysis when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in treating, preventing, or managing osteolysis when compared to the administration of vitamin C or $K_3$ alone.

Without being limited by any theory, a synergistic effect of the combination of vitamins C and K permits the use of lower dosages of vitamin C and/or K, and/or less frequent administration of the combination to a subject with a condition, disorder, or disease. The ability to utilize lower dosages of the combination (e.g., a prophylactic or therapeutic agent) and/or to administer the combination less frequently reduces the toxicity associated with the administration of the combination to a subject without reducing the efficacy of the combination in the prevention or treatment of a condition, disorder, or disease. In addition, a synergistic effect can result in improved efficacy of vitamin C and/or K in the prevention or treatment of a condition, disorder, or disease. Furthermore, a synergistic effect of the combination may avoid or reduce adverse or unwanted side effects associated with the use of either vitamin C or K alone.

In another embodiment, provided herein is a method of treating, preventing, or managing inflammation associated with a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In one embodiment, the inflammation is associated with particulate debris from the prosthetic implant in the subject. In certain embodiments, the combination of vitamins C and K has a synergetic effect in treating, preventing, or managing inflammation associated with the prosthetic implant when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in treating, preventing, or managing inflammation associated with a prosthetic implant when compared to the administration of vitamin C or $K_3$ alone.

In yet another embodiment, provided herein is a method of treating joint disorder in a subject, which comprises surgically replacing the hip or joint of the subject, and chronically administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof.

In yet another embodiment, provided herein is a method of treating, preventing, or managing inflammation caused by a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In one embodiment, the inflammation is caused by particulate debris from the prosthetic implant in the subject. In certain embodiments, the combination of vitamins C and K has a synergetic effect in treating, preventing, or managing inflammation caused by the prosthetic implant when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in treating, preventing, or managing inflammation caused by a prosthetic implant when compared to the administration of vitamin C or $K_3$ alone.

In yet another embodiment, provided herein is a method of increasing the functional life of a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the combination of vitamins C and K has a synergetic effect in increasing the functional life of the prosthetic implant when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in increasing the functional life of the prosthetic implant when compared to the administration of vitamin C or $K_3$ alone.

In still another embodiment, provided herein is a method of treating, preventing, or managing NFκB-mediated condition, disorder, or disease caused by a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the method of treating, preventing, or managing NFκB-mediated condition, disorder, or disease is caused by particulate debris from a prosthetic implant in the subject. In certain embodiments, the combination of vitamins C and K has a synergetic effect in treating, preventing, or managing NFκB-mediated condition, disorder, or disease in a subject when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in treating, preventing, or managing NFκB-mediated condition, disorder, or disease in a subject when compared to the administration of vitamin C or $K_3$ alone.

In one embodiment, the NFκB-mediated condition, disorder, or disease is inflammation. In another embodiment, the NFκB-mediated condition, disorder, or disease is osteolysis. In yet another embodiment, the NFκB-mediated condition, disorder, or disease is aseptic osteolysis. In yet another embodiment, the NFκB-mediated condition, disorder, or disease is osteolysis caused by inflammation.

Vitamin C and/or K as used in the methods provided herein can be delivered as a single dose such as, e.g., a single bolus injection, or as a single oral tablet or pill.

In one embodiment, vitamins C and K as used in the methods provided herein are formulated in a single unit dosage form. In another embodiment, vitamins C and K are each formulated separately in its own single unit dosage form. In one embodiment, vitamins C and K are formulated in a pharmaceutical composition as discussed herein.

In certain embodiments, vitamin C and/or K as used in the methods provided herein can be administered over time, such as, e.g., continuous infusion over time or divided bolus doses over time.

Vitamin C and/or K as used in the methods provided herein can be administered once daily (QD), or divided into multiple daily doses such as twice daily (BID), three times daily (TID), four times daily (QID), five times daily, six times daily, seven times daily, eight times daily, nine times daily, or ten times daily. In addition, the administration can be continuous, i.e., every day, or intermittently. The term "intermittent" or "intermittently" as used herein is intended to mean stopping and starting at either regular or irregular intervals. For example, intermittent administration of the compound provided herein is administration for one to six days per week, administration in cycles (e.g., daily administration for two to eight consecutive weeks, then a rest period with no administration for up to one week), or administration on alternate days.

In certain embodiments, vitamin C and/or K as used in the methods provided herein is administered from about 1 to about 20 times a day, from about 1 to about 15 times a day, from about 1 to about 10 times a day, or from about 1 to about 5 times a day. In certain embodiments, vitamin C and/or K as used in the methods provided herein is administered every 1 to 10 hour(s), every 2 to 8 hours, every 3 to 7 hours, every 4 to 6 hours, or every 5 to 6 hours. In certain embodiments, vitamin C and/or K in the methods provided herein is administered every hour, every 2 hours, every 3 hours, every 4 hours, every 5 hours, every 6 hours, every 7 hours, every 8 hours, every 9 hours, or every 10 hours. In certain embodiments, vitamin C and/or K as used in the methods provided herein is administered once a day. In certain embodiments, vitamin C and/or K as used in the methods provided herein is administered 5 times a day. In certain embodiments, vitamin C and/or K as used in the methods provided herein is administered 10 times a day. In certain embodiments, vitamin C and/or K as used in the methods provided herein is administered every 4, 5, or 6 hours.

In certain embodiments, vitamin C as used in the methods provided herein is administered to the subject in the amount ranging from about 1 to about 1,000 mg/kg/day, from about 5 to about 500 mg/kg/day, or from about 10 to about 100 mg/kg/day. In certain embodiments, vitamin C as used in the methods provided herein is administered to the subject in the amount of about 10 mg/kg/day, about 20 mg/kg/day, about 30 mg/kg/day, about 40 mg/kg/day, about 50 mg/kg/day, about 60 mg/kg/day, about 70 mg/kg/day, about 80 mg/kg/day, about 90 mg/kg/day, about 100 mg/kg/day, about 200 mg/kg/day, about 300 mg/kg/day, about 400 mg/kg/day, or about 500 mg/kg/day.

In certain embodiments, vitamin K as used in the methods provided herein is administered to the subject in the amount ranging from about 0.01 to about 50 mg/kg/day, from about 0.015 to about 50 mg/kg/day, from about 0.05 to about 40 mg/kg/day, from about 0.2 to about 30 mg/kg/day, or from about 10 to about 30 mg/kg/day. In certain embodiments, vitamin K as used in the methods provided herein is administered to the subject in the amount of about 0.015 mg/kg/day, about 5 mg/kg/day, about 25 mg/kg/day, or about 30 mg/kg/day.

The administered dose of vitamin C and/or K can also be expressed in units other than the unit "mg/kg/day" or "g/kg/day." For example, doses for parenteral administration can be expressed as mg/m$^2$/day. One of ordinary skill in the art would readily know how to convert doses from mg/kg/day to mg/m$^2$/day to given either the height or weight of a subject or both (See, www.fda.gov/cder/cancer/animal-frame.htm).

In certain embodiments, vitamin C as used in the methods provided herein is administered to the subject in the amount ranging from about 0.1 g to about 3 g every four hours. In certain embodiments, vitamin K as used in the methods provided herein is administered to the subject in the amount ranging from about 0.2 mg to about 300 mg given every four hours.

In certain embodiments, vitamin C as used in the methods provided herein is administered to the subject in the amount ranging from about 500 mg to about 3,000 mg a day. In certain embodiments, vitamin K as used in the methods provided herein is administered to the subject in the amount ranging from about 3 mg to about 30 mg a day. In certain embodiments, vitamin C as used in the methods provided herein is administered to the subject in the amount ranging from about 2,000 mg to about 3,000 mg a day; and vitamin K is administered to the subject in the amount ranging from about 12 mg to about 19 mg a day. In certain embodiments, vitamin C as used in the methods provided herein is administered to the subject in the amount ranging from about 2,000 mg to about 3,000 mg a day; and vitamin K is administered to the subject in the amount ranging from about 20 mg to about 30 mg a day.

In certain embodiments, vitamin C as used in the methods provided herein is administered to the subject in the amount of about 2,000 mg a day; and vitamin K is administered to the subject in the amount of about 12 mg a day. In certain embodiments, vitamin C as used in the methods provided herein is administered to the subject in the amount of about 3,000 mg a day; and vitamin K is administered to the subject in the amount of about 19 mg a day.

In certain embodiments, vitamin C as used in the methods provided herein is administered to the subject in the amount of about 2,000 mg a day; and vitamin K is administered to the subject in the amount of about 20 mg a day. In certain embodiments, vitamin C as used in the methods provided herein is administered to the subject in the amount of about 3,000 mg a day; and vitamin K is administered to the subject in the amount of about 30 mg a day.

In certain embodiments, vitamins C and K are administered as one or more capsules, each comprising about 500 mg of sodium L-ascorbate and about 3 mg of sodium 1,2,3,4-tetrahydro-2-methyl-1,4-dioxo-2-naphthalene sulfonate.

In certain embodiments, vitamins C and K are administered as one or more capsules, each comprising about 500 mg of sodium L-ascorbate and about 5 mg of sodium 1,2,3,4-tetrahydro-2-methyl-1,4-dioxo-2-naphthalene sulfonate.

Depending on the condition, disorder, or disease to be treated and the subject's condition, vitamin C and/or K in the methods provided herein can be administered by oral, parenteral (e.g., intramuscular, intraperitoneal, intravenous, CIV, intracistemal injection or infusion, subcutaneous injection, or implant), inhalation, nasal, vaginal, rectal, sublingual, or topical (e.g., transdermal or local) routes of administration. Vitamin C and/or K in the methods provided herein may be formulated, alone or together, in suitable dosage unit with pharmaceutically acceptable excipients, carriers, adjuvants and vehicles, appropriate for each route of administration.

In one embodiment, vitamin C is administered orally. In another embodiment, vitamin C is administered parenterally. In yet another embodiment, vitamin C is administered intravenously.

In one embodiment, vitamin K is administered orally. In another embodiment, vitamin K is administered parenterally. In yet another embodiment, vitamin K is administered intravenously.

The routes of administration of vitamins C and K can be the same or different. In certain embodiments, both vitamins C and K are administered orally.

In one embodiment, vitamin C is administered concurrently with vitamin K. In another embodiment, vitamin C is administered separately with vitamin K. In yet another embodiment, vitamin C is administered sequentially with vitamin K. In yet another embodiment, vitamin C is administered before vitamin K. In yet another embodiment, vitamin C is administered after vitamin K. Each of the above is encompassed within the term of "in combination with."

In certain embodiments, a combination of 1,000 mg of vitamin C and 10 mg of vitamin $K_3$ is administered to the subject twice a day (2,000 mg of vitamin C and 20 mg of vitamin $K_3$ per day). In certain embodiments, a combination of 1,000 mg of vitamin C and 10 mg of vitamin $K_3$ is administered to the subject twice a day for 13 weeks.

In certain embodiments, a combination of 1,000 mg of vitamin C and 6.2 mg of vitamin $K_3$ is administered to the subject twice a day (2,000 mg of vitamin C and 12.4 mg of vitamin $K_3$ per day). In certain embodiments, a combination of 1,000 mg of vitamin C and 6.2 mg of vitamin $K_3$ is administered to the subject twice a day for 13 weeks.

In certain embodiments, a daily dose of 5,000 mg of vitamin C and 50 mg of vitamin $K_3$ is administered to the subject.

In certain embodiments, vitamin C and vitamin $K_3$ are administered at the levels of 5 g/m$^2$/day and 50 mg/m$^2$/day, respectively. In certain embodiments, vitamin C and vitamin $K_3$ are administered at the levels of 5 g/m$^2$/day and 50 mg/m$^2$/day, respectively, for 7 days.

In certain embodiments, a combination of vitamin C and vitamin $K_3$ is administered to the subject after mealtime.

In certain embodiments, the prosthetic particulate debris comprises micrometer, submicrometer, or nanometer particles. In certain embodiments, the prosthetic particulate debris contains polymers. In certain embodiments, the prosthetic particulate debris contains polyethylene. In certain embodiments, the prosthetic particulate debris contains conventional ultrahigh molecular weight polyethylene (UHMWPE) or highly crosslinked polyethylene (XLPE). In certain embodiments, the prosthetic particulate debris contains ceramic, alumina, or zirconia. In certain embodiments, the prosthetic particulate debris contains metal. In certain embodiments, the prosthetic particulate debris contains cobalt (Co), chromium (Cr), molybdenum (Mo), manganese (Mn), titanium (Ti), aluminum (Al), vanadium (V), iron (Fe), nickel (Ni), indium (In), tantalum (Ta), zirconium (Zr), niobium (Nb), or a mixture thereof, which is to include different surface stoichiometric compositions. In certain embodiments, the prosthetic particulate debris comprises Co, Cr, and Mo.

In certain embodiments, the surface of the prosthetic particulate debris contains polymers. In certain embodiments, the surface of the prosthetic particulate debris contains polyethylene. In certain embodiments, the surface of the prosthetic particulate debris contains conventional ultrahigh molecular weight polyethylene (UHMWPE) or highly crosslinked polyethylene (XLPE). In certain embodiments, the surface of the prosthetic particulate debris contains metal. In certain embodiments, the surface of the prosthetic particulate debris contains cobalt (Co), chromium (Cr), molybdenum (Mo), manganese (Mn), titanium (Ti), aluminum (Al), vanadium (V), iron (Fe), nickel (Ni), indium (In), tantalum (Ta), zirconium (Zr), niobium (Nb), or a mixture thereof, which is to include different surface stoichiometric compositions. In certain embodiments, the surface of the prosthetic particulate debris comprises Co, Cr, and Mo.

In certain embodiments, the subject is a mammal. In certain embodiments, the mammal is a human.

The methods provided herein encompass treating a subject regardless of patient's age, although some conditions, diseases, or disorders are more common in certain age groups. In certain embodiments, the subject is a male. In certain embodiments, the subject is a female. In certain embodiments, the subject is an elderly. Elderly men and women are further defined below.

In certain embodiments, the subject is a human with an age of no less than about 20 years, no less than about 30 years, no less than about 40 years, no less than about 45 years, no less than about 50 years, no less than about 55 years, no less than about 60 years, no less than about 65 years, no less than about 70 years, or no less than about 80 years. In certain embodiments, the subject is a human with an age of above about 60, above about 65, above about 70, or above about 75. In certain embodiments, the subject is a human with an age ranging from about 20 to about 30 years, from about 30 to about 40 years, from about 40 to about 50 years, from about 50 to about 60 years, from about 60 to about 70 years, or from about 70 to about 80 years. In certain embodiments, the subject is a human with an age ranging from about 20 to about 110 years, from about 30 to about 100 years, from about 40 to about 100 years, from about 50 to about 100 years, from about 50 to about 95 years, from about 50 to about 90 years, or from about 50 to about 85 years.

In certain embodiments, the subject has osteopenia. In certain embodiments, the subject has osteoporosis. In certain embodiments, the subject has osteoarthritis. In certain embodiments, the subject has rheumatoid arthritis. In certain embodiments, the subject has a cancerous joint or bone disease. In certain embodiments, the subject has hormonal or drug induced bone loss. In certain embodiments, the subject has loss of bone mass (density) due to zero gravity conditions (space travel).

In certain embodiments, the subject has a prosthetic implant. In certain embodiments, the subject does not have a prosthetic implant. Examples of prosthetic implants include, but are not limited to, prosthetic hip, knee, shoulder, elbow, wrist, ankle, the small bones of the wrist, thumb, hand, foot, and temparomandibular joints, and intervertebral disk joint of the spine replacement. In one embodiment, the prosthetic implant is prosthetic hip replacement. In another embodiment, the prosthetic implant is prosthetic knee replacement. In yet another embodiment, the prosthetic implant is prosthetic shoulder replacement. In certain embodiments, the subject has predisposition for metal sensitivity/hypersensitivity reaction.

In certain embodiments, the subject is treated with at least one of the methods provided herein before prosthetic implant operation. In certain embodiments, the subject is treated with at least one of the methods provided herein during prosthetic implant operation. In certain embodiments, the subject is treated with at least one of the methods provided herein after prosthetic implant operation. In certain embodiments, the subject is treated as maintenance therapy after surgery with at least one of the methods provided herein. In certain embodiments, the subject is treated immediately after surgery with at least one of the methods provided herein. In certain embodiments, the subject is treated regularly, e.g. chronically, including for about 1 year, about 2 years, about 3 years, about 4 years, or more than 4 years after surgery with at least one of the methods provided herein.

In certain embodiments, the subject to be treated with one of the methods provided herein has not been treated with any of the methods provided herein. In certain embodiments, the subject to be treated with one of the methods provided herein has been treated with one of the methods provided herein.

The combination regimen can be administered repetitively if necessary, for example, until the patient experiences stable disease or regression, or until the patient experiences disease progression or unacceptable toxicity. Stable disease or lack thereof is determined by methods known in the art such as evaluation of patient symptoms, physical examination, visualization of the site of the prosthetic implant that has been imaged using X-ray, CAT, PET, MRI scan, or analyses of patient's blood (venous puncture) or synovial fluid aspiration.

In certain embodiments, the combination regimen is for acute use or short term use, e.g., during the period of the onset of the condition, disorder, or disease described herein. In certain embodiments, the combination regimen is for chronic use or long term use, e.g., before, after, and during the period of the onset of the condition, disorder, or disease described herein.

In certain embodiments, the combination regimen is administered to the subject over an extended period of time, ranging from about 1 day to about 50 years, from about 10 days to about 25 years, from about 1 month to about 10 years, from about 6 months to about 5 years. In certain embodiments, the combination regimen is administered to the subject for about 12 weeks. In certain embodiments, the combination regimen is administered to the subject for about 6 months. In certain embodiments, the combination regimen is administered to the subject for about 1 year. In certain embodiments, the combination regimen is administered to the subject for about 2 years.

In certain embodiments, the combination regimen is cyclically administered to the subject. Cycling therapy involves the administration of the combination regimen provided herein for a period of time, followed by a rest for a period of time, and repeating this sequential administration.

As used herein, the term "combination regimen" includes the use of more than one therapies (e.g., one or more prophylactic and/or therapeutic agents). However, the use of the term "combination regimen" does not restrict the order in which therapies (e.g., prophylactic and/or therapeutic agents) are administered to the subject. A first therapy (e.g., a prophylactic or therapeutic agent such as vitamin C provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as vitamin K) to the subject.

The methods provided herein may further comprise administering an additional therapeutic agent useful in the treatment and/or prevention of a condition, disorder, or disease described herein.

In triple therapy, effective dosages of therapeutic agents can be administered together, alternatively, or sequentially. The dosages given will depend on absorption, inactivation, and excretion rates of the therapeutic agents as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Examples of the additional therapeutic agent include, but are not limited to, anti-atherosclerotic agents, such as ACAT inhibitors; antibiotics, such as anthracyclines, bleomycins, mitomycin, dactinomycin, and plicamycin; anticoagulants, such as acenocoumarol, argatroban, bivalirudin, lepirudin, fondaparinux, heparin, phenindione, warfarin, and ximelagatran; antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, indomethacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; antiproliferatives, such as methotrexate, FK506 (tacrolimus), and mycophenolate mofetil; anti-TNF antibodies or soluble TNF receptor, such as etanercept, rapamycin, and leflunimide; aP2 inhibitors; beta-adrenergic agents, such as carvedilol and metoprolol; bile acid sequestrants, such as questran; calcium channel blockers, such as amlodipine besylate; chemotherapeutic agents; bisphosphonates, such as alendronate, risendronate, ibandtonate, pamidronate, and etidronate; cyclooxygenase-2 (COX-2) inhibitors, such as celecoxib and rofecoxib; cyclosporins; cytotoxic drugs, such as azathioprine and cyclophosphamide; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; endothelin converting enzyme (ECE) inhibitors, such as phosphoramidon; enzymes, such as L-asparaginase; Factor VIIa Inhibitors and Factor Xa Inhibitors; farnesyl-protein transferase inhibitors; fibrates; growth factor inhibitors, such as modulators of PDGF activity; growth hormone secretagogues; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; hormonal agents, such as glucocorticoids (e.g., hydrocortisone and cortisone), estrogens/antiestrogens, androgens/antiandrogens, progestins, and luteinizing hormone-releasing hormone antagonists, and octreotide acetate; immunosuppressants; mineralocorticoid receptor antagonists, such as spironolactone and eplerenone; microtubule-disruptor agents, such as ecteinascidins; microtubule-stabilizing agents, such as pacitaxel, docetaxel, and epothilones A-F; MTP Inhibitors; niacin; phosphodiesterase inhibitors, such as PDE III inhibitors (e.g., cilostazol) and PDE V inhibitors (e.g., sildenafil, tadalafil, and vardenafil); plant-derived products, such as vinca alkaloids, epipodophyllotoxins, and taxanes; platelet activating factor (PAF) antagonists; platinum coordination complexes, such as cisplatin, satraplatin, and carboplatin; potassium channel openers; prenyl-protein transferase inhibitors; protein tyrosine kinase inhibitors; protein serine/threonine inhibitors; renin inhibitors; squalene synthetase inhibitors; steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; TNF-alpha inhibitors, such as tenidap; thrombin inhibitors, such as hirudin; thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); thromboxane receptor antagonists, such as ifetroban; topoisomerase inhibitors; vasopeptidase inhibitors (dual NEP-ACE inhibitors), such as omapatrilat and gemopatrilat; and other miscellaneous agents, such as, hydroxyurea, procarbazine, mitotane, hexamethylmelamine, and gold compounds.

In one embodiment, provided herein is a method of reducing NFκB production in a cell exposed to prosthetic particulate debris, comprising contacting the cell with a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the combination of vitamins C and K has a synergetic effect in reducing NFκB production when compared to the administration of vitamin C or K alone.

In another embodiment, provided herein is a method of reducing a cytokine level in a cell exposed to prosthetic particulate debris, comprising contacting the cell with a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the combination of vitamins C and K has a synergetic effect in reducing the cytokine level when compared to the administration of vitamin C or K alone. In one embodiment, the cytokine is IL-6.

In yet another embodiment, provided herein is a method of reducing a chemokine level in a cell exposed to prosthetic particulate debris, comprising contacting the cell with a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the combination of vitamins C and K has a synergetic effect in reducing the chemokine level when compared to the administration of vitamin C or K alone. In one embodiment, the chemokine is IL-8.

In yet another embodiment, provided herein is a method of enhancing proliferation of a cell exposed to prosthetic particulate debris, comprising contacting the cell with a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the combination of vitamins C and K has a synergetic effect in enhancing cell proliferation when compared to the administration of vitamin C or K alone.

In certain embodiments, the cell is a mammalian cell. In certain embodiments, the mammal is a human cell. In certain embodiments, the cell is a fibroblast. In certain embodiments, the cell is a human fibroblast. In certain embodiments, the cell is a synovial fibroblast. In certain embodiments, the cell is a human synovial fibroblast. In certain embodiments, the cell is a human macrophage, T lymphocyte, or B lymphocyte.

In certain embodiments, the cell is treated by contacting the cell with vitamin C, prior to contacting the cell with vitamin K. In certain embodiments, the cell is treated by contacting the cell with vitamin C, concurrently with vitamin K. In certain embodiments, the cell is treated by contacting the cell with vitamin C, after contacting the cell with vitamin K.

The cell proliferation can be gauged by, e.g., counting the number of cells contacted with compounds of interest, comparing the cell proliferation with otherwise identical cells not contacted with the compounds. The number of cells, as well as the size of the cells, can be readily assessed using any method known in the art (e.g., trypan blue exclusion and cell counting, 3-[4,5-dimethylthiazol-2-yl]-2,5-diphenyltetrazolium bromide assay (MTT), and measuring incorporation of $^3$H-thymidine into nascent DNA in a cell).

The combination regimes provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes containers and dosage forms of the compounds in the combination regimens provided herein.

In certain embodiments, the kit includes a container comprising dosage forms of the compounds in the combination regimens provided herein, in one or more containers.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

Example 1

Effect of Prosthetic Particulate Debris on Human Synovial Fibroblasts

Two different sources of metallic particulate powders, CoCrMo—I and CoCrMo—II, each having a size smaller than 10 μm, were used in this example. These powders were ASTM F75 grade material, which is commonly used in joint replacement prostheses. Energy dispersive spectroscopy (ESD) was used to determine the bulk metallic composition, and X-ray photoelectron spectroscopy (XPS) was used to determine the surface metallic composition of the particles. The results are summarized in Table 1. While multiple EDS area scans identified the bulk metallic compositions of the powders to resemble the ASTM F75 CoCrMo standard, multiple XPS survey scans demonstrated that the surface metallic compositions were different.

Using an experimental protocol approved by the Institutional Review Board Committee on Human Research, a cell culture study was performed, exposing human synovial fibroblasts to CoCrMo—I and CoCrMo—II, in order to assess any effects the different materials might have on cellular viability. The cells were harvested from tissue of the knee joint of four consented human volunteer donors undergoing a total knee replacement. The harvested tissue was processed as described (Mostardi et al., *J. Biomed. Mater. Res.* 1999, 47, 60; and Mostardi et al., *J. Biomed. Mater. Res.* 2002, 59, 605), passaging each donor cell line once prior to being transferred to multiple 25 cm$^2$ culture flasks. The fibroblasts in each culture flask were then allowed to grow to confluency (a single-cell layer that occupies a give area; 1×10$^6$ cells per flask) before experimental powder exposure.

TABLE 1

|  | CoCrMo-I | | CoCrMo-II | | F75 CoCrMo[c] |
|---|---|---|---|---|---|
|  | EDS[a] | XPS[b] | EDS[a] | XPS[b] | ASTM Standard |
| Co | 62% | 30% | 62% | 69% | 57.4-65% |
| Cr | 34% | 30% | 32% | 28% | 27-30% |
| Mo | 3% | 5% | 4% | 3% | 5-7% |
| Si | 1% | 27% | 2% | 0% | ≤1% |
| Mn | 0% | 8% | 0% | 0% | ≤1% |

[a]Experimental uncertainty is 2%.
[b]Experimental uncertainty is <5%.
[c]Standards as published by the American Society for testing Materials.

Prior to their exposure to the confluent fibroblast cultures, the CoCrMo—I and CoCrMo—II powders were sterilized and verified to be endotoxin free by a limulus amebocyte lysate assay. Two mass dosage (0.004 g and 0.04 g) of each metal powder to induce a minimal and a maximal cytotoxic effect, respectively, were individually added to separate culture flasks containing each donor cell line. In addition, culture flasks from each donor cell line, to which no metal powder was added, were used as confluent controls.

Five days after the exposure dosages of each metal powder to the culture flasks, cell viability counts were made from each culture flask using hemocytometer and trypan blue exclusion (counting the number of viable cells which have not taken up the dye color). The resulting viability counts were first normalized by counts from their respective, non-challenged, control flasks and then were averaged over all four donors to create a composite mean and standard deviation for each metal powder sample.

The type of metal powder used exhibited a significant effect on the cellular viability ($p<0.0001$). Fibroblast exposure to the 0.004 g dosage of CoCrMo—I powder resulted in a nominal 11% reduction in viability, where the same exposure dosage of CoCrMo—II powder resulted in an 86% reduction in viability. Differences in effects on fibroblast viability were even more apparent at the higher 0.04 dosage, with the CoCrMo—I powder resulting in a moderate 30% reduction in viability and the CoCrMo—II powder resulting in a 97% reduction in viability. See, Kovacik et al., *Colloids and Surface B: Biointerfaces* 2008, 65, 269-275.

Example 2

Effect of Vitamins C and K3 on Human Synovial Fibroblasts Exposed to Metal Particles A metal exposure dosage of 0.01 g (CoCrMo—I as described in Example 1) was used for all cell exposure studies in this example. APATONE® was prepared in a 100:1 ratio (75.0 µM of vitamin C (sodium L-ascorbate) and 0.75 µM of chromium-free vitamin $K_3$ (vitamin $K_3$ sodium bisulfite)).

Human synovial fibroblasts were harvested and processed as described in Example 1. The donor cell line was passaged once prior to the seeding of about $1\times10^6$ cells into each of ten 75 cm$^2$ culture flasks. The flasks were then incubated over a 5-day period to render about $5\times10^6$ cells. Five of the flasks were incubated for 24 hrs and consisted of: a) control (cell only), b) cell treated with APATONE® only, c) cells exposed to metal only, d) cells treated with APATONE® for 24 hrs prior to metal exposure, and e) cells exposed to metals 24 hrs prior to APATONE® treatment. The remaining five flasks, prepared in the same manner, were incubated for a 48 hr interval.

Flasks at each of the respective time interval (24 hr or 48 hr) were assessed for cell viability (hemocytometer with trypan blue exclusion) and NFκB levels (EZ-Detect NFκB p65 Transcription Assay, Thermo Fisher Scientific, Rockford, Ill.). The results are summarized in Table 2.

TABLE 2

|  | Cell Viability | | NFκB Level | |
| --- | --- | --- | --- | --- |
|  | 24 hrs | 48 hrs | 24 hrs | 48 hrs |
| APATONE | 1.04 | 1.67 | 1.20 | 0.79 |
| F75 CoCrMo | 1.12 | 1.10 | 1.49 | 0.94 |
| APATONE ® then F75 CoCrMo | 1.06 | 1.17 | 0.49 | 0.58 |
| F75 CoCrMo then APATONE ® | 1.06 | 1.08 | 1.09 | 0.31 |

Since fibroblast viability was 104% of the control at 24 hrs and 167% of the control at 48 hrs, APATONE® was not toxic to the fibroblasts at this dose. Fibroblast viability remained relatively constant following exposure to the metal with 112% and 110% viability compared to control fibroblasts after 24 and 48 hrs, respectively. Fibroblast viability was 106% and 117% when the fibroblasts were exposed to APATONE® 24 hrs before the metal. The increase in cell viability at 48 hrs was probably due to APATONE® induced cell division of the fibroblasts. As was the case for metal treatment alone, fibroblast viability remained constant 106% and 108% when APATONE® treatment followed metal treatment.

When synovial fibroblasts were treated with APATONE®, NFκB levels rose to 120% of control by 24 hrs and then decreased to 79% of control by 48 hrs. Exposure of fibroblasts to the metal led to an increase of NFκB levels to 149% of control by 24 hrs. NFκB levels returned to 95% of control by 48 hrs. Pretreatement of fibroblasts with APATONE® before exposure to metal resulted in NFκB levels to 49% of control by 24 hrs. NFκB levels rose to 58% of control by 48 hrs. Administration of APATONE® following metal exposure produced a slight increase in NFκB levels to 109% of control by 24 hrs. NFκB levels then decreased to 31% of control by 48 hrs.

Example 3

Effect of Vitamins C and K3 on Human Synovial Fibroblasts Exposed to Metal Particles A metal exposure dosage of 0.01 g (CoCrMo—I and CoCrMo—II as described in Example 1) was used for all cell exposure studies in this example. APATONE® was prepared as described in Example 2.

Human synovial fibroblasts were harvested and processed as described in Example 1. The synovial fibroblasts were seeded into 6 culture flasks and incubated to render about $5\times10^6$ cells in each. For each metal, three flasks were incubated for 24 hrs and consisted of: a) control (cell only), b) cells exposed to metal only, and cells exposed to metal 24 hrs prior to treatment with APATONE®.

Figure 2:
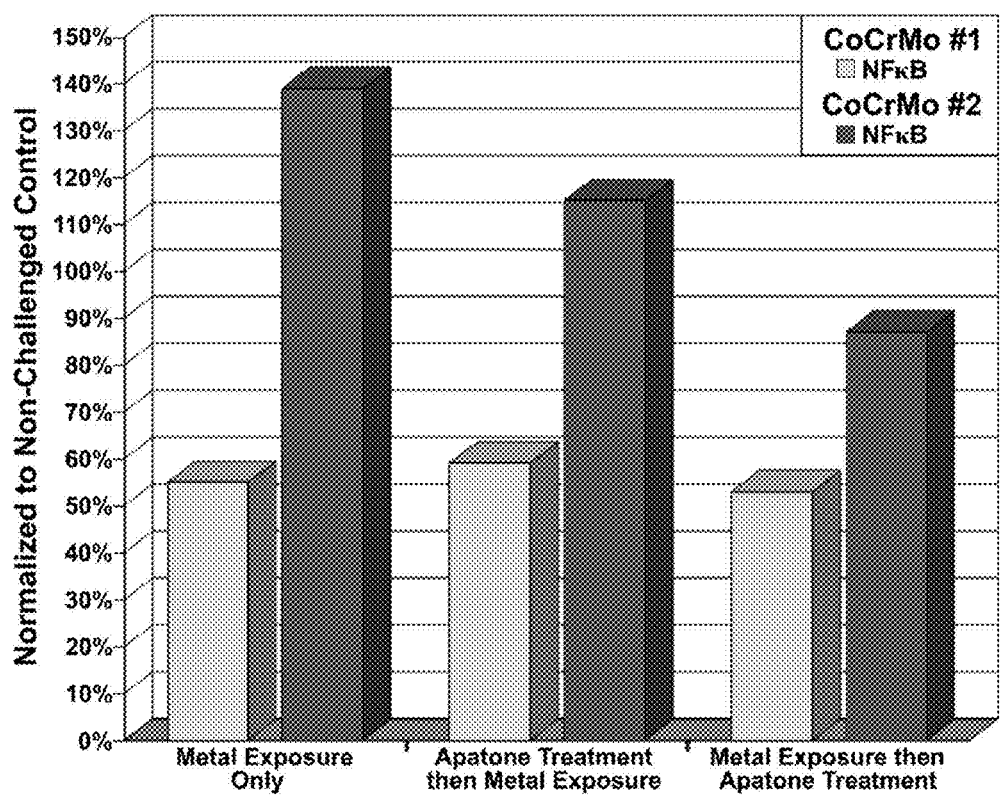
FIG. 2 shows the effect of APATONE® on NFκB levels in human synovial fibroblasts exposed to metal particles.
Figure 3:
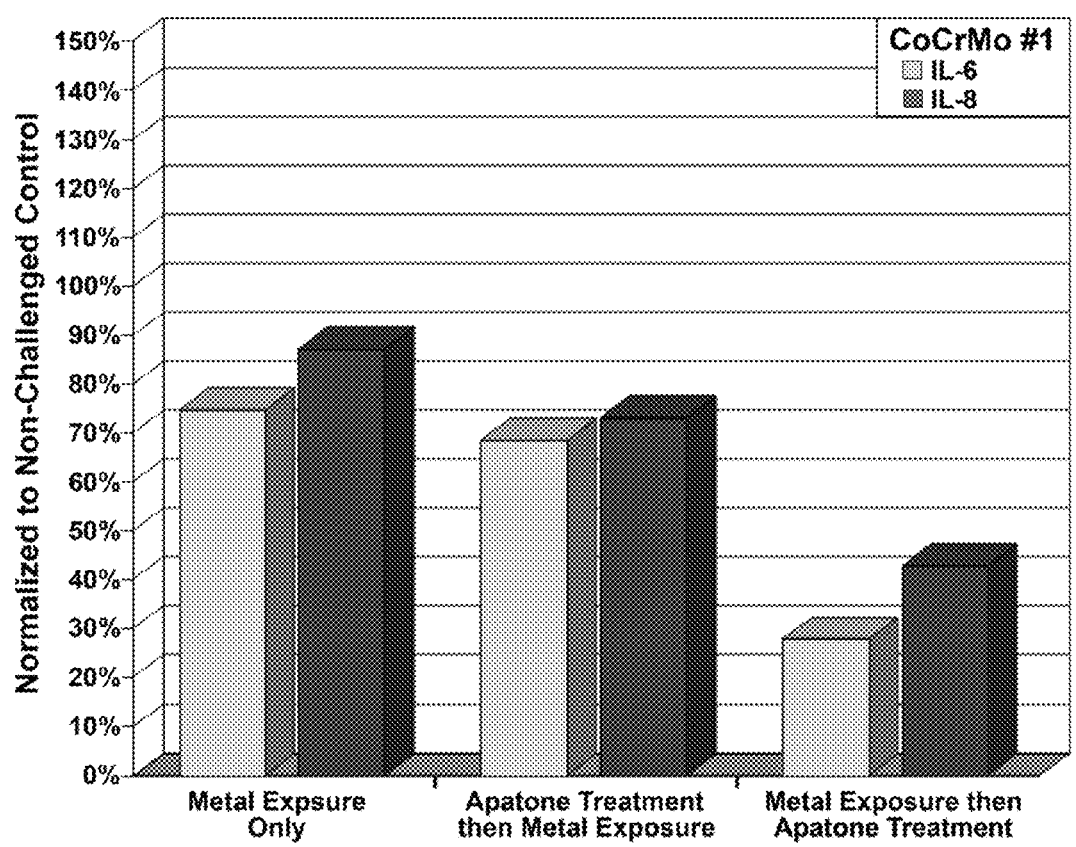
FIG. 3 shows the effect of APATONE® on cytokine/chemokine levels in human synovial fibroblasts exposed to metal particles.

Each culture flask was assessed for cellular viability, NFκB, cytokine (IL-6) and chemokine (IL-8) levels (LUMINEX® 200 xMAP platform, MiraiBio Group, South San Francisco, Calif.). The results are shown in FIGS. 1, 2, and 3.

Example 4

Cytotoxicity of APATONE® Against Human Dermal Fibroblasts

APATONE® was evaluated by 3-[4,5-dimethylthiazol-2-yl]-2,5-diphenyltetrazolium bromide assay (MTT). HS68 fibroblasts were used in this Example. Results are summarized in Tables 3 to 5.

TABLE 3

| Vitamins Alone | | | |
| --- | --- | --- | --- |
| Incubation (days) | Sodium L-Ascorbate $CD_{50}$ (µM) | Mg L-Ascorbate $CD_{50}$ (µM) | $VK_3$ $CD_{50}$ (µM) |
| 1 | 1468 | 1663 | 18.7 |
| 2 | 1245 | 1746 | 19.0 |
| 3 | 1185 | 1501 | 18.7 |

TABLE 4

| Incubation (days) | Sodium L-Ascorbate | | Mg L-Ascorbate | |
|---|---|---|---|---|
| | VC CD$_{50}$ (μM) | VK$_3$ CD$_{50}$ (μM) | VC CD$_{50}$ (μM) | VK$_3$ CD$_{50}$ (μM) |
| 1 | 458 | 4.7 | 382 | 3.8 |
| 2 | 471 | 4.7 | 383 | 3.8 |
| 3 | 471 | 4.7 | 342 | 3.4 |

$^a$The ratio of vitamin C to Vitamin K$_3$ is 100.

TABLE 5

| Incubation (days) | Sodium L-Ascorbate | | Mg L-Ascorbate | |
|---|---|---|---|---|
| | VC CD$_{50}$ (μM) | VK$_3$ CD$_{50}$ (μM) | VC CD$_{50}$ (μM) | VK$_3$ CD$_{50}$ (μM) |
| 1 | 466 | 2.3 | 392 | 3.8 |
| 2 | 467 | 2.3 | 348 | 1.7 |
| 3 | 397 | 2.0 | 193 | 1.0 |

$^a$The ratio of vitamin C to Vitamin K$_3$ is 200.

Example 5

Capsule Formulation (1,000 mg Vitamin C and 10 mg Chromium-Free Vitamin K$_3$)

For 100 capsules, sodium ascorbate powder (100 g) and water soluble chromium-free vitamin K$_3$ (menadione sodium bisulfte) powder (1.0 g) are mixed together. The mixture is then placed into capsules in the amount of 1,010 mg each, without any supplementary ingredients or any pharmaceutically acceptable excipients.

Example 6

Capsule Formulation (500 mg Vitamin C and 5 mg Chromium-Free Vitamin K$_3$)

For 100 capsules, sodium ascorbate powder (50 g) and water soluble chromium-free vitamin K$_3$ (menadione sodium bisulfte) powder (0.5 g) are mixed together. The mixture is then placed into capsules in the amount of 505 mg each, without any supplementary ingredients or any pharmaceutically acceptable excipients.

Example 7

Capsule Formulation (500 mg Vitamin C and 3.1 mg Chromium-Free Vitamin K$_3$)

For 100 capsules, sodium ascorbate powder (50 g) and water soluble chromium-free vitamin K$_3$ (menadione sodium bisulfte) powder (0.31 g) are mixed together. The mixture is then placed into capsules in the amount of 503.1 mg each, without any supplementary ingredients or any pharmaceutically acceptable excipients.

Example 8

Capsule Formulation (200 mg Vitamin C and 2 mg Chromium-Free Vitamin K$_3$)

For 100 capsules, sodium ascorbate powder (20 g) and water soluble chromium-free vitamin K$_3$ (menadione sodium bisulfte) powder (0.3 g) are mixed together. The mixture is then placed into capsules in the amount of 202 mg each, without any supplementary ingredients or any pharmaceutically acceptable excipients.

Example 9

Tablet Formulation (500 mg Vitamin C and 5 mg Chromium-Free Vitamin K$_3$)

For 100 tablets, sodium ascorbate powder (50 g) and water soluble chromium-free vitamin K$_3$ (menadione sodium bisulfte) powder (0.5 g) are mixed together with microcrystalline cellulose.

Example 10

Parenteral Dosage Formulation (5 g Vitamin C and 50 mg Chromium-Free Vitamin K$_3$)

A vitamin C solution is prepared by dissolving sodium ascorbate (5 g) and NaCl (1.2 g) in sterile water (300 mL) for injection. A chromium-free vitamin K$_3$ solution is prepared by dissolving chromium-free menadione sodium bisulfite (50 mg) in sterile water (5 mL) for injection.

These solutions must be oxygen-free (e.g., perfused with gaseous nitrogen); sterilized by filtration (millipore filters of pore diameter approximately 0.22 nm); and introduced into sterile and devoid of oxygen pockets for the vitamin C solution or glass vials for vitamin K$_3$ solution. Each series of prepared pockets or vials must be examined for apyrogenicity and sterility by methods known in the art. Since both vitamins are oxygen, light, and temperature sensitive, the solutions should be stored in anoxic conditions at approximately 4° C. in darkness.

Alternately, the parenteral solution is prepared by mixing sodium ascorbate (5 g) and chromium-free menadione sodium bisulfite (50 mg) in 300 mL of sterile non-pyrogenic normal saline in an IV bag immediately prior to use.

Example 11

Capsule Formulation (1,000 mg Vitamin C and 10 mg Chromium-Free Vitamin K$_3$)

For 100 capsules, sodium ascorbate powder (100 g) and water soluble chromium-free vitamin K$_3$ (menadione sodium bisulfte, with ≤2 ppm Cr) powder (1.0 g) are mixed together. The mixture is then placed into capsules in the amount of 1,010 mg each, without any supplementary ingredients or any pharmaceutically acceptable excipients.

Example 12

Capsule Formulation (500 mg Vitamin C and 5 mg Chromium-Free Vitamin K$_3$)

For 100 capsules, sodium ascorbate powder (50 g) and water soluble chromium-free vitamin K$_3$ (menadione sodium bisulfte, with ≤2 ppm Cr) powder (0.5 g) are mixed together. The mixture is then placed into capsules in the amount of 505 mg each, without any supplementary ingredients or any pharmaceutically acceptable excipients.

Example 13

Capsule Formulation (500 mg Vitamin C and 3.1 mg Chromium-Free Vitamin K$_3$)

For 100 capsules, sodium ascorbate powder (50 g) and water soluble chromium-free vitamin K$_3$ (menadione sodium bisulfte, with ≤2 ppm Cr) powder (0.31 g) are mixed together. The mixture is then placed into capsules in the amount of 503.1 mg each, without any supplementary ingredients or any pharmaceutically acceptable excipients.

Example 14

Capsule Formulation (200 mg Vitamin C and 2 mg Chromium-Free Vitamin $K_3$)

For 100 capsules, sodium ascorbate powder (20 g) and water soluble chromium-free vitamin $K_3$ (menadione sodium bisulfte, with ≤2 ppm Cr) powder (0.3 g) are mixed together. The mixture is then placed into capsules in the amount of 202 mg each, without any supplementary ingredients or any pharmaceutically acceptable excipients.

Example 15

Tablet Formulation (500 mg Vitamin C and 5 mg Chromium-Free Vitamin $K_3$)

For 100 tablets, sodium ascorbate powder (50 g) and water soluble chromium-free vitamin $K_3$ (menadione sodium bisulfte, with ≤2 ppm Cr) powder (0.5 g) are mixed together with microcrystalline cellulose.

Example 16

Parenteral Dosage Formulation (5 g Vitamin C and 50 mg Chromium-Free Vitamin $K_3$)

A vitamin C solution is prepared by dissolving sodium ascorbate (5 g) and NaCl (1.2 g) in sterile water (300 mL) for injection. A vitamin $K_3$ solution is prepared by dissolving chromium-free menadione sodium bisulfite (50 mg, ≤2 ppm Cr) in sterile water (5 mL) for injection.

These solutions must be oxygen-free (e.g., perfused with gaseous nitrogen); sterilized by filtration (millipore filters of pore diameter approximately 0.22 nm); and introduced into sterile and devoid of oxygen pockets for the vitamin C solution or glass vials for vitamin $K_3$ solution. Each series of prepared pockets or vials must be examined for apyrogenicity and sterility by methods known in the art. Since both vitamins are oxygen, light, and temperature sensitive, the solutions should be stored in anoxic conditions at approximately 4° C. in darkness.

Alternately, the parenteral solution is prepared by mixing sodium ascorbate (5 g) and chromium-free menadione sodium bisulfite (50 mg, ≤2 ppm Cr) in 300 mL of sterile non-pyrogenic normal saline in an IV bag immediately prior to use.

Example 17

Treatment of Ostelysis in Patients Using Vitamins C and $K_3$

Patient A:

Female patient A at age 56 had bilateral total knee arthroplasties (TKA) using a cobalt-chromium-molybdenum (CoCrMo) knee system. Four months after TKA, Patient A developed progressive swelling and pain in both her knees. Six months after TKA, Patient A was unable to return to work and began receiving disability.

During her postoperative care, Patient A was prescribed a nonsteroidal anti-inflammatory to which the knees were somewhat responsive. Over the course of treatment, multiple knee aspirations were performed with no evidence of infection. Blood labs revealed all parameters fell within normal ranges, except for an elevated C-Reactive Protein and Rheumatoid Factor.

Patient A was evaluated for inflammatory arthritis, but was found not to have rheumatoid. Suspecting a possible prosthetic metal sensitivity, specimens were sent to a medical facility in Chicago for metal sensitivity analyses about a year after TKA. A proliferation assay and cytomatic analysis revealed that Patient A had a moderate degree (5-fold) of lymphocyte hyper-reactivity to nickel (Ni) and a 3-fold lymphocyte hyperreactivity to chromium (Cr). Recommendation was to revise the CoCrMo component system to a zirconium (Zr) component system.

About 18 months after TKA, Patient A received a revised Zr TKA system in her left knee by a second orthopedic surgeon. However, following the surgery both knees continued to become increasingly more painful to the touch with marked swelling. About seven years after the first TKA, Patient A estimated her functional active range of motion (aROM) for both knees was around 10° (0, 10).

About eight years after the first TKA, APATONE® (vitamin C 500 mg+chromium-free vitamin $K_3$ 3.1 mg) was administered to Patient A (two tablets, twice daily). Approximately 10-days later, Patient A's condition was unchanged. Because Patient A had developed diarrhea and associated it with APATONE®, she had temporarily stopped taking APATONE®. Approximately six-weeks later and after having continued taking APATONE®, Patient A's condition was much improved. By the time of her first refill, the swelling in both knees was markedly reduced with significant pain relief. During this time period, Patient A developed significant neck discomfort in the area where she had previously had instrumented neck surgery about more year ago; this discomfort was most likely masked by her knee pain. Concerned of a reaction to the metal used for her neck surgery, Patient A's dosage of APATONE® was increased to 3 tablets, twice daily. Following the dosage increase, Patient A's neck pain was completely resolved within a few weeks. Her swelling had completely resolved. After the APATONE® treatment, Patient A had a little more than 60° of flexion with full extension in her left knee and a little more than 50° of flexions with full extension in her right knee.

Patient B:

Male Patient B at age 63 had unilateral total knee arthroplasties (TKA) of the right knee using a cobalt-chromium-molybdenum (CoCrMo)/(TiAlV) knee system. One year later, Patient B elected to undergo a second elective unilateral total knee arthroplasty of the contralateral (left) knee using the same knee system. Over the course of the last seven years, Patient B had developed significant patellofemoral pain of the left knee and moderate overall pain of the right knee. Recently, Patient B had an episode in which he fell from a curb and impacted his left knee. Under the care of a second treating orthopaedic surgeon, it was recommended that a left total knee revision procedure be scheduled for a possible loose patellar component. Alternatively it was suggested by the original surgeon to first attempt APATONE® therapy of a suspected inflammatory response to the prostheses. Patient B started on an oral dosage of Vitamin C and $K_3$ (two capsules taken twice daily of Vitamin C 500 mg+chromium-free Vitamin $K_3$ 5 mg).

During the office evaluation prior to taking the Vitamin C and $K_3$ supplement, Patient B was bilaterally evaluated using a standard SF36 questionnaire, visual analog scales, the Hospital for Surgery Knee Score (HSS) and the Knee Society Knee Score (KSS). Using visual analog scales (100 mm), Patient B described his current bilateral knee pain as 50, his current functional capacity as 32, and his current energy level as 26. Patient B's general health was described as "fair' and somewhat worse than one year prior. His current condition limited most activities commonly attempted during a typical day (vigorous activity, carrying groceries, stair climbing, bending/kneeling, bathing, etc.). Over the last month, his condition caused him to cut down on the "amount of time" spent on work or activities, he stated that he "accomplished less", he was limited in the "kind" of work or activities, and that he had "difficulty" performing work or activities. On average his left knee pain while walking and at rest was described as "moderate," while the right knee pain was described as "mild." Patient B had an active range of motion (ROM) of 107° (8° extension lag, 115 flexion) in the left knee and 118 of ROM (0° extension lag, 118 flexion) in the right knee. His overall HSS score for the left knee was poor (60.4), while the right knee was good (83.8). Similarly, his overall KSS pain score of the left knee was 44.4 and for KSS function was 50, while the right knee scored 93.6 for pain and 100 for function.

After taking the oral APATONE® for approximately 3-months, Patient B's overall health had dramatically improved. Patient B stated that his bilateral knee pain had significantly improved and that overall his general health had improved and he currently felt he had a greater energy level (participated in the actual move from his home to a condo). A more recent office evaluation showed joint improvement by his treating orthopaedic surgeon, his treating surgeon again delayed scheduling a revision surgery, and instead a second script for an Vitamin C and K₃ was refilled.

After the APATONE® treatment, Patient B was bilaterally evaluated using a standard SF36 questionnaire, visual analog scales, the Hospital for Surgery Knee Score (HSS) and the Knee Society Knee Score (KSS). The visual analog scales (100 mm) showed improvements in his current bilateral knee pain, described as 60, his current functional capacity as 60, and his current energy level as 80. While still suffering discomfort in the left knee, the patient's general health was now described as "good" and much better than 6-months prior. His latest condition was less limiting in performing most activities commonly attempted during a typical day. Patient B stated he was just digging in the garden for three hours the day before this evaluation. Over the last month, his condition had not caused him to cut down on the "amount of time" spent on work or activities, he stated that he no longer "accomplished less", he was not limited in the "kind" of work or activities, and that he did not have as much "difficulty" performing work or activities. On average his left knee pain while walking and at rest was still described as "moderate", the right knee pain had improved to "none" or no pain, and "mild", respectively. He could extend the left knee fully and had an active range of motion (ROM) of approximately 110° (0° extension lag, 110° flexion), while his right knee continued to have approximately 120° of ROM (0° extension lag, 120 flexion). His overall HSS score for the left knee had improved somewhat from a score of 60.4 to 66.8 but was still considered poor, while the right knee had improved to excellent (92). Similarly, his overall KSS pain score of the left knee had improved by 15.6 points (from 44.4 to 60) and for the KSS function had improved by 30 points (from 50 to 80), while the right knee had also improved with a score of 99 for pain and 100 for function. While the left knee had improved, the continual moderate pain suggests that the impact injury he sustained earlier might have fractured the patella or loosened the patellar component, a condition that can only be concluded by operative evaluation.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating or managing osteolysis in a subject, comprising administering to the subject a therapeutically effective amount of: (i) ascorbic acid, or a pharmaceutically acceptable salt, solvate, or hydrate thereof; and (ii) 2-methyl-1,4-naphthalenedione, or a pharmaceutically acceptable solvate or hydrate thereof.

2. The method of claim 1, wherein the osteolysis is aseptic osteolysis.

3. The method of claim 1, wherein the osteolysis is caused by inflammation or a prosthetic implant in the subject.

4. The method of claim 3, wherein the prosthetic implant is one selected from prosthetic hip, knee, shoulder, elbow, wrist, ankle, the small bones of the wrist, thumb, hand, foot, and temparomandibular joints, and intervertebral disk joint of the spine replacement.

5. The method of claim 3, wherein the prosthetic implant is a joint replacement, or a knee or hip replacement.

6. The method of claim 3, wherein the osteolysis is caused by particulate debris from the prosthetic implant in the subject.

7. The method of claim 6, wherein the prosthetic particulate debris comprises a metal.

8. The method of claim 7, wherein the metal is cobalt, chromium, molybdenum, manganese, silicon, titanium, aluminum, or vanadium, or a mixture thereof.

9. The method of claim 1, wherein the subject is a human.

10. The method of claim 1, wherein (i) the ascorbic acid, or a pharmaceutically acceptable salt, solvate, or hydrate thereof is administered orally; or (ii) 2-methyl-1,4-naphthalenedione, or a pharmaceutically acceptable solvate or hydrate thereof is administered orally.

11. The method of claim 1, wherein (i) the ascorbic acid, or a pharmaceutically acceptable salt, solvate, or hydrate thereof; and (ii) 2-methyl-1,4-naphthalenedione, or a pharmaceutically acceptable solvate or hydrate thereof are administered together in a single composition.

12. The method of claim 1, wherein (i) the ascorbic acid, or a pharmaceutically acceptable salt, solvate, or hydrate thereof; and (ii) 2-methyl-1,4-naphthalenedione, or a pharmaceutically acceptable solvate or hydrate thereof are formulated together in a single oral dosage form.

13. The method of claim 12, wherein the single oral dosage form is provided as a tablet or capsule.

14. The method of claim 12, wherein the single oral dosage form is provided as a capsule.

15. The method of claim 14, wherein the capsule contains (i) about 500 mg of the ascorbic acid, or a pharmaceutically acceptable salt, solvate, or hydrate thereof; and (ii) about 5 mg of 2-methyl-1,4-naphthalenedione, or a pharmaceutically acceptable solvate or hydrate thereof.

16. The method of claim 14, wherein the capsule consists essentially of (i) the ascorbic acid, or a pharmaceutically acceptable salt, solvate, or hydrate thereof; and (ii)

2-methyl-1,4-naphthalenedione, or a pharmaceutically acceptable solvate or hydrate thereof.

17. The method of claim 1, wherein the ascorbic acid, or a pharmaceutically acceptable salt, solvate, or hydrate thereof is L-ascorbic acid or a pharmaceutically acceptable salt thereof, or a pharmaceutically acceptable solvate or hydrate thereof.

18. The method of claim 17, wherein the ascorbic acid, or a pharmaceutically acceptable salt, solvate, or hydrate thereof is an alkali or alkaline earth metal salt of L-ascorbic acid, or a pharmaceutically acceptable solvate or hydrate thereof.

19. The method of claim 17, wherein the ascorbic acid, or a pharmaceutically acceptable salt, solvate, or hydrate thereof is sodium, potassium, calcium, or magnesium L-ascorbate, or a pharmaceutically acceptable solvate or hydrate thereof.

20. The method of claim 1, wherein the weight ratio of the ascorbic acid to 2-methyl-1,4-naphthalenedione is ranging from about 50 to about 500.

21. The method of claim 20, wherein the weight ratio of the ascorbic acid to 2-methyl-1,4-naphthalenedione is about 100.

22. The method of claim 1, wherein (i) the ascorbic acid, or a pharmaceutically acceptable salt, solvate, or hydrate thereof is administered in the amount ranging from about 500 mg to about 3,000 mg per day; and (ii) 2-methyl-1,4-naphthalenedione, or a pharmaceutically acceptable solvate or hydrate thereof is administered in the amount ranging from about 3 mg to about 30 mg per day.

23. The method of claim 22, wherein (i) the ascorbic acid, or a pharmaceutically acceptable salt, solvate, or hydrate thereof is administered in the amount of about 2,000 mg or about 3,000 mg per day; and (ii) 2-methyl-1,4-naphthalenedione, or a pharmaceutically acceptable solvate or hydrate thereof is administered in the amount of about 12 mg to about 19 mg per day.

24. A method of increasing the functional life of a prosthetic implant in a subject, comprising administering to the subject a therapeutically effective amount of (i) ascorbic acid, or a pharmaceutically acceptable salt, solvate, or hydrate thereof; and (ii) 2-methyl-1,4-naphthalenedione, or a pharmaceutically acceptable solvate or hydrate thereof.

25. The method of claim 14, wherein the capsule contains (i) about 1,000 mg of the ascorbic acid, or a pharmaceutically acceptable salt, solvate, or hydrate thereof; and (ii) about 10 mg of 2-methyl-1,4-naphthalenedione, or a pharmaceutically acceptable solvate or hydrate thereof.

* * * * *